(12) United States Patent
Fu et al.

(10) Patent No.: US 7,247,617 B2
(45) Date of Patent: Jul. 24, 2007

(54) SIXTEEN-MEMBER MACROLIDE ANTIINFECTIVE AGENTS

(75) Inventors: Hong Fu, Union City, CA (US);
Leonard Katz, Oakland, CA (US);
David C. Myles, Kensington, CA (US)

(73) Assignee: Kosan Biosciences Incorporated, Hayward, CA (US)

( * ) Notice: Subject to any disclaimer, the term of this patent is extended or adjusted under 35 U.S.C. 154(b) by 114 days.

(21) Appl. No.: 11/154,435

(22) Filed: Jun. 15, 2005

(65) Prior Publication Data
US 2006/0014707 A1  Jan. 19, 2006

Related U.S. Application Data

(60) Provisional application No. 60/632,853, filed on Dec. 2, 2004, provisional application No. 60/587,974, filed on Jul. 13, 2004.

(51) Int. Cl.
*A61K 31/70* (2006.01)
*C07H 17/08* (2006.01)

(52) U.S. Cl. .......................................... 514/30; 536/7.1

(58) Field of Classification Search ................. 536/7.1; 514/30
See application file for complete search history.

(56) References Cited

U.S. PATENT DOCUMENTS

| | | | |
|---|---|---|---|
| 3,459,853 A | 8/1969 | Gorman et al. | |
| 3,784,447 A | 1/1974 | Theriault | |
| 4,321,361 A | 3/1982 | Baltz et al. | |
| 4,918,058 A | 4/1990 | Lukacs et al. | |
| 5,023,240 A | 6/1991 | Narandja et al. | |
| 5,140,014 A | 8/1992 | Maring et al. | |
| 5,545,624 A | 8/1996 | Hecker et al. | |
| 5,677,287 A | 10/1997 | Jaynes | |
| 5,688,924 A | 11/1997 | Narandja et al. | |
| 5,922,684 A | 7/1999 | Narandja et al. | |
| 6,680,299 B2 | 1/2004 | Or et al. | |
| 2002/0128213 A1 | 9/2002 | Katz et al. | |
| 2004/0014687 A1 | 1/2004 | Ma et al. | |

FOREIGN PATENT DOCUMENTS

| | | |
|---|---|---|
| EP | 0070170 A1 | 1/1983 |
| EP | 0287082 A2 | 4/1987 |
| EP | 0410433 A2 | 1/1991 |
| EP | 0985679 A1 | 3/2000 |
| JP | 62-221695 A | 9/1987 |
| WO | WO 2005/118610 A2 | 12/2005 |

OTHER PUBLICATIONS

Debono et al., J. Antibiotics 42 (8), 1253-1267 (1989), "Synthesis and Antimicrobial Evaluation of 20-Deoxo-20-(3,5-dimethylpiperidin-1-ylo)desmycosin (Tilmicosin, EL-870) and Related Cyclic Amino Derivatives".
Grandjean et al., J. Carbohydrate Chem. 15 (7), 831-855 (1996), "SN2 Displacement of Carbohydrate Triflates by 9-Oximes of Erythromycin A and of a Tylosin Derivative".
Maring et al., J. Antibiotics 44 (4), 448-450 (1991), "Synthesis and Antimicrobial Activities of 9(S)-N,N-Dimethyl-amino-9-deoxo-10,11,12,13,-tetrahydroniddamycin".
Narandja et al., J. Antibiotics 52 (1), 68-70 (1999), "New Derivatives of Tylosin IV. Dihydro and Tetrahydro Desmycosin Oximes".
Ruggeri et al., J. Antibiotics 42 (9), 1443-1445 (1989), "Synthesis and Antibacterial Activity of 9-O-[(2-Methoxy-Demycarosyltylosin)".
Sakamoto et al., J. Antibiotics 37 (12), 1628-1634 (1984), "Synthesis of 23-Deoxy-23-N-ethyl-23-(2-fluoro-, 2,2-difluoro-, and 2,2,2-trifulorethyl)amino Derivative of Myca-minosyl Tylonolide and 4'-Deoxymycaminosyl Tylonolide".
Tanaka et al., J. Antibiotics 35 (1), 113-116 (1982), "Synthesis of 23-Dialkylamino Derivatives of Mycaminosyl Tylonolide and 4'-Deoxymycominosyl Tylonolide Effective Against Gram-Negative Bacteria".
Wermuth, ed., *The Practice of Medicinal Chemistry*, 2nd Ed., pp. 561-586 (Academic Press 2003), "Designing Prodrugs and Bioprecursors".

*Primary Examiner*—Elli Peselev
(74) *Attorney, Agent, or Firm*—Yuan Chao

(57) ABSTRACT

Sixteen membered macrolide anti-infective agents having a structure according to formula I

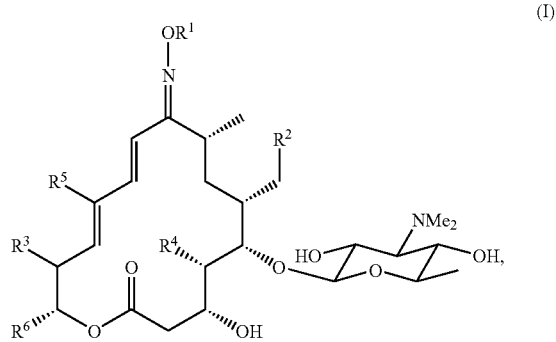

where $R^1$, $R^2$, $R^3$, $R^4$, $R^5$, and $R^6$ are as defined herein, and related compounds are disclosed.

27 Claims, 5 Drawing Sheets

SIXTEEN-MEMBER MACROLIDE ANTIINFECTIVE AGENTS

CROSS-REFERENCE TO RELATED APPLICATIONS

Figure 1:
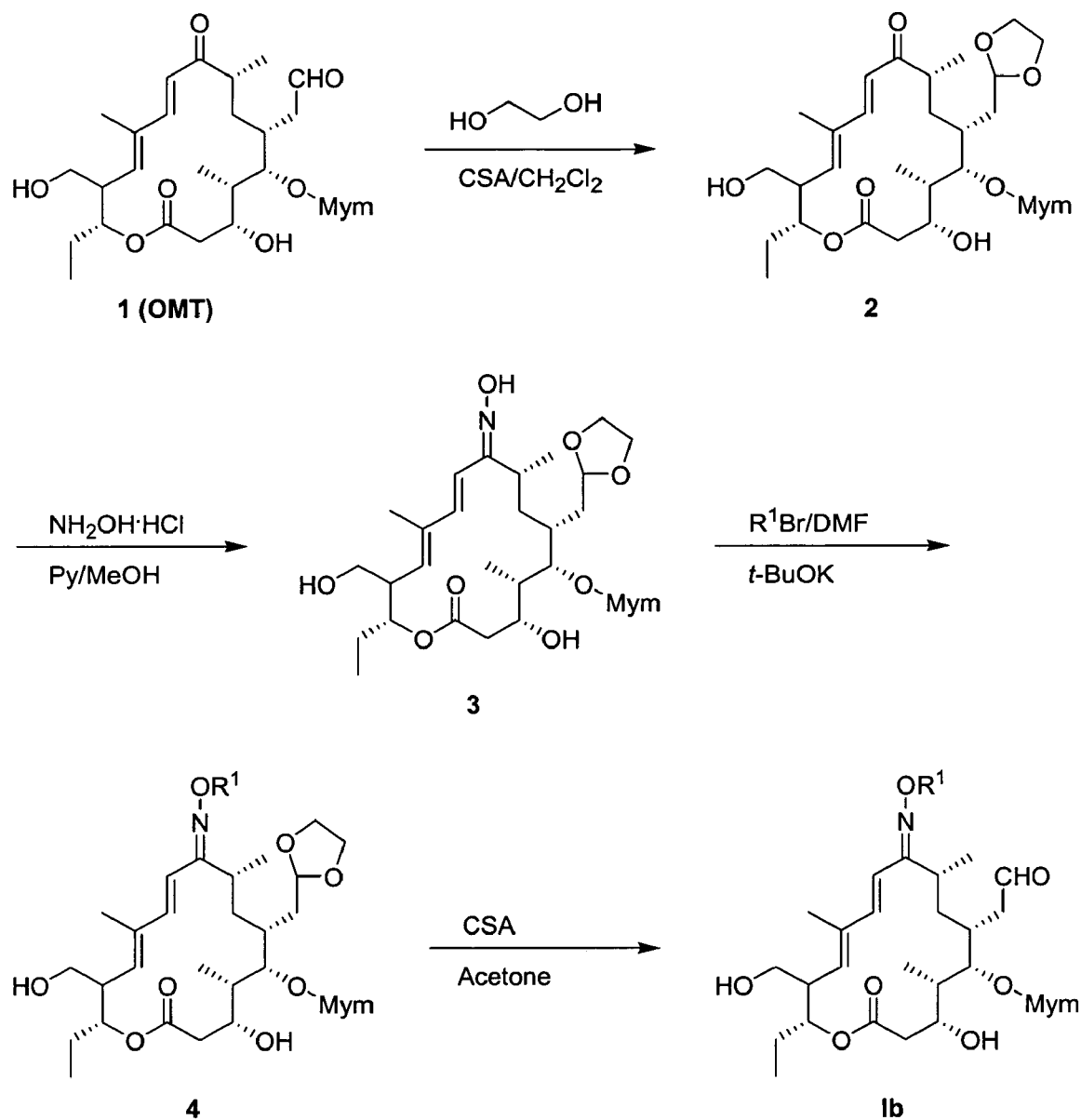

This application claims the benefit under 35 U.S.C. § 119(e) of U.S. Provisional Applications Nos. 60/587,974, filed Jul. 13, 2004, and 60/632,853, filed Dec. 2, 2004, the disclosures of which are incorporated herein by reference.

BACKGROUND OF THE INVENTION

1. Field of the Invention

This invention relates to 16-membered macrolide antiinfective agents and methods for making and using them.

2. Description of Related Art

Both 14- and 16-membered macrolide antibiotics have been used extensively in human and veterinary medicine. These compounds bind to bacterial ribosomes and inhibit protein synthesis. Erythromycin A, the prototype 14-membered macrolide antibiotic, has a limited activity spectrum and unpleasant gastrointestinal side effects due to an acid catalyzed rearrangement resulting in the creation of derivatives that have high affinity for the motilin receptor. These issues have prompted a large effort in the design of semi-synthetic analogs of erythromycin A, leading to compounds such as clarithromycin (Biaxin™), azithromycin (Zithromax™), and the more recently developed ketolides, telithromycin (Ketek™) and cethromycin (ABT773).

In addition to the efforts in the 14-membered macrolide area, there have been considerable efforts in the 16-membered macrolide area. Illustrative disclosures relating to semi-synthetic 16-membered macrolide antibiotics include: Theriault, U.S. Pat. No. 3,784,447 (1974); Gorman et al., U.S. Pat. No. 3,459,853 (1969); Lukacs et al., U.S. Pat. No. 4,918,058 (1990); Narandja et al., U.S. Pat. No. 5,023,240 (1991); Maring et al., U.S. Pat. No. 5,140,014 (1992); Hecker et al., U.S. Pat. No. 5,545,624 (1996); Jaynes, U.S. Pat. No. 5,677,287 (1997); Narandja et al., U.S. Pat. No. 5,688,924 (1997); Narandja et al., U.S. Pat. No. 5,922,684 (1999); Or et al., U.S. Pat. No. 6,680,299 B2 (2004); Katz et al., US 2002/0128213 A1 (2002); Ma et al., US 2004/0014687 A1 (2004); Hamao et al., EP 0,070,170 A1 (1983); Narandja et al., EP 0,287,082 (1988); Lopotar et al., EP 0,410,433 A2 (1991); Narandja et al., EP 0,985,679 A1 (2000); Hamao et al., JP 62-221695 A (1987); Tanaka et al., *J. Antibiot.* 35 (1), 113-116 (1982); Sakamoto et al., *J. Antibiot.* 37 (12), 1628-1634 (1984); Debono et al., *J. Antibiot.* 42 (8), 1253-1267 (1989); Ruggeri et al., *J. Antibiot.* 42 (9), 1443-1445 (1989); Maring et al., *J. Antibiot.* 44 (4), 448-450 (1991); Grandjean et al., *J. Carbohydrate Chem.*, 15 (7), 831-855 (1996); and Narandja et al., *J. Antibiot.* 52 (1), 68-70 (1999); the disclosures of which are incorporated herein by reference.

Due to the continuing emergence of antibiotic-resistant bacterial strains, there exists an ongoing need for new antibacterial compounds. We have discovered new 16-member macrolide antibacterial compounds having a useful spectrum of activity against various bacteria.

BRIEF SUMMARY OF THE INVENTION

In a first aspect, this invention provides a compound having a structure according to formula I

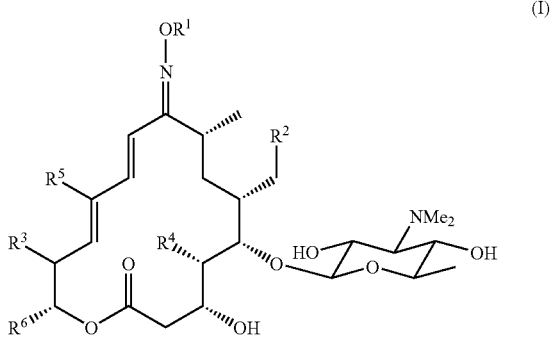

(I)

and the pharmaceutically acceptable salts, esters, solvates, hydrates, and prodrug forms thereof, wherein $R^1$ is H,

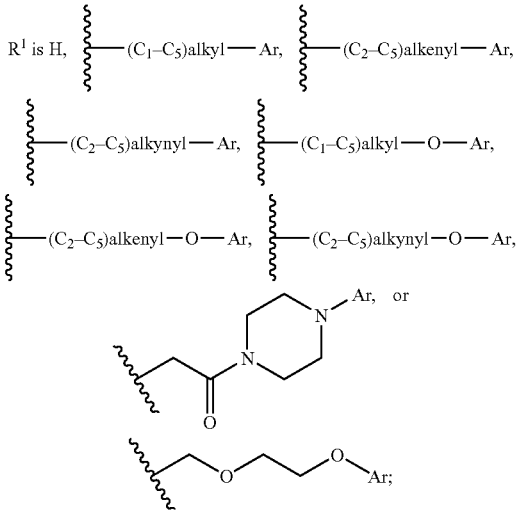

$R^2$ is CHO or

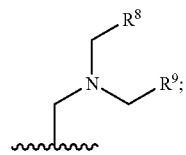

$R^3$ is H, $CH_2OH$,

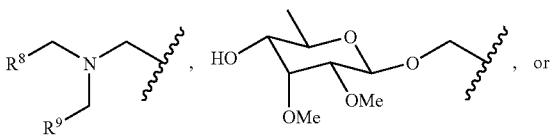

-continued

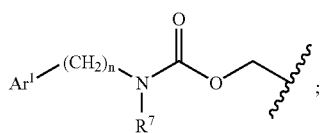

$R^4$ is MeO or Me;
$R^5$ is H or Me;
$R^6$ is Me or Et;
$R^7$ is H or $C_1$-$C_4$ alkyl;
$R^8$ and $R^9$ are independently H, $(C_1$-$C_4)$alkyl, $CH_2OH$, or $CH_2O(C_1$-$C_4)$alkyl, or $R^8$ and $R^9$ combine to form $(CHR^{10})_m$;
each $R^{10}$ is independently H, OH, $O(C_1$-$C_4)$alkyl, or $(C_1$-$C_4)$alkyl;
Ar is an unsubstituted or substituted aromatic moiety selected from the group consisting of phenyl,

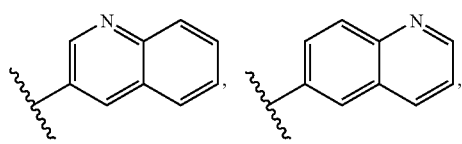

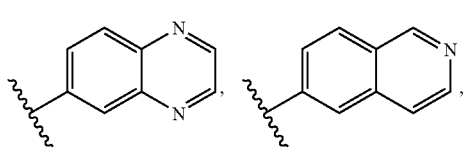

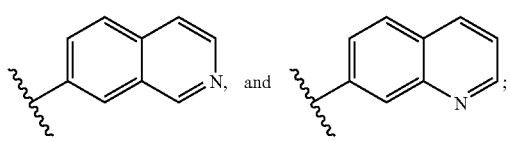

wherein a substituted aromatic moiety Ar has one to three substituents independently selected from the group consisting of halo, hydroxy, $C_1$-$C_4$ alkyl, $C_2$-$C_4$ alkenyl, $C_2$-$C_4$ alkynyl, trifluoromethyl, cyano, nitro, $C_1$-$C_3$ alkylamino or dialkylamino, and $C_1$-$C_3$ alkoxy; and $Ar^1$ is phenyl or phenyl substituted with one to three substituents independently selected from the group consisting of halo, hydroxy, $C_1$-$C_4$ alkyl, $C_2$-$C_4$ alkenyl, $C_2$-$C_4$ alkynyl, trifluoromethyl, cyano, nitro, $C_1$-$C_3$ alkylamino or dialkylamino, and $C_1$-$C_3$ alkoxy;
m is 1, 2, 3, or 4; and
n is 0, 1, or 2;
subject to
a first proviso (I) that when (a) $R^1$ is other than

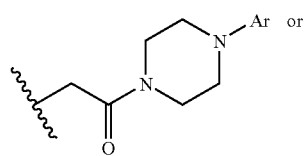

(b) $R^2$ is CHO, and (c) $R^3$ is other than

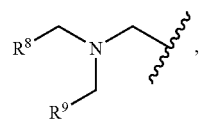

then Ar is other than unsubstituted or substituted phenyl; and a second proviso (II) that when (a) $R^1$ is H and (b) $R^2$ is CHO, then $R^3$ is

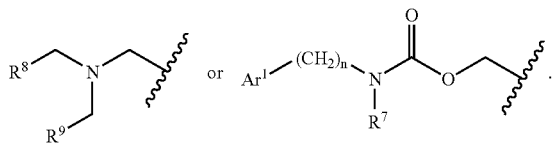

In a second aspect, there is provided a compound having a structure according to formula IIa, IIb, IIc, or IId:

(IIa)

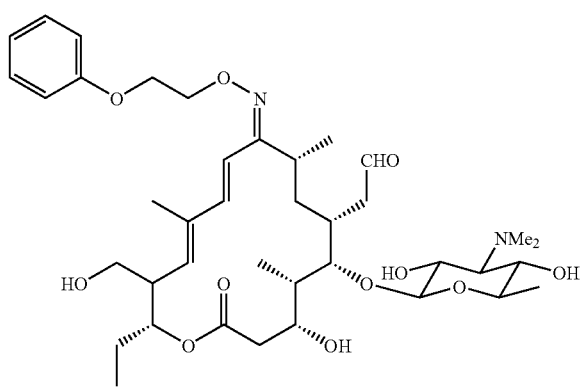

(IIb)

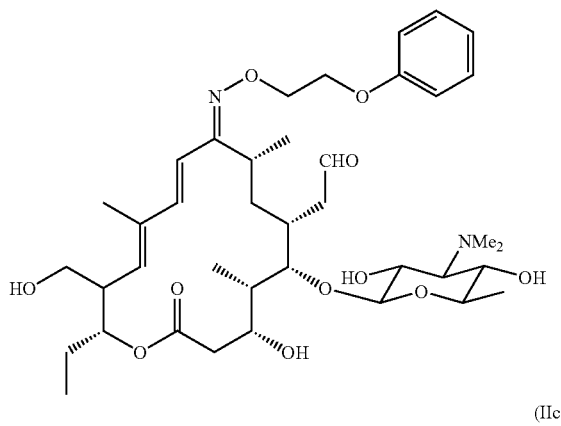

(IIc)

(IId)

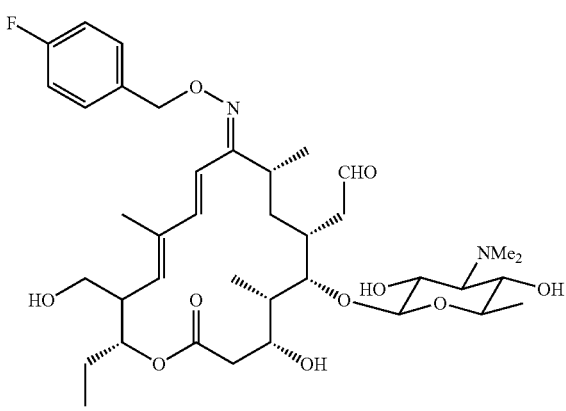

and the pharmaceutically acceptable salts, solvates, hydrates, and prodrug forms thereof.

In a third aspect, there is provided a method for treating a bacterial infection, comprising administering to a patient suffering from such infection a therapeutically effective amount of a compound of this invention.

In a fourth aspect, there is provided the use of a compound of this invention for the preparation of a medicament for treating a bacterial infection.

In a fifth aspect, there is provided a pharmaceutical formulation comprising a compound of this invention and an excipient.

In a sixth aspect, there is provided a method for inhibiting the proliferation of bacteria, comprising contacting the bacteria with an effective amount of a compound of this invention. Such contacting may take place in vitro or in vivo.

BRIEF DESCRIPTION OF THE DRAWING(S)

FIGS. 1 through 5 show schemes for the synthesis of compounds of this invention.

DETAILED DESCRIPTION OF THE INVENTION

Definitions

"Alkyl" means an optionally substituted straight or branched chain hydrocarbon moiety having the specified number of carbon atoms in the chain (e.g., as in "$C_1$-$C_5$ alkyl") or, where the number of carbon atoms is not specified, up to 3 carbon atoms in the chain.

"Alkenyl" means an optionally substituted straight or branched chain hydrocarbon moiety having at least one carbon-carbon double bond and the specified number of carbon atoms in the chain (e.g., as in "$C_2$-$C_5$ alkenyl") or, where the number of carbon atoms is not specified, up to 3 carbon atoms in the chain.

"Alkynyl" means an optionally substituted straight or branched chain hydrocarbon moiety having at least one carbon-carbon triple bond and the specified number of carbon atoms in the chain (e.g., as in "$C_2$-$C_5$ alkynyl") or, where the number of carbon atoms is not specified, up to 3 carbon atoms in the chain.

"Alkoxy" means an alkyl group bonded to oxygen, as in methoxy or ethoxy.

"Alkylamino" means an alkyl group bonded to an amine nitrogen, as in methyl amino. "Dialkylamino" means two alkyl groups (which may be the same or different) bonded to the same amine nitrogen, as in dimethylamino.

"Halogen" or "halo" means fluorine, chlorine, bromine or iodine.

"Mym" means a mycaminosyl group, represented by one of the structures below, according to whether it is used in a monovalent or divalent context:

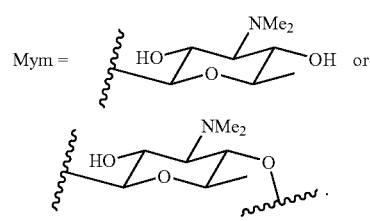

"Myn" means a mycinosyl group, represented by the structure below:

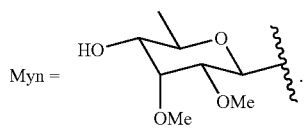

"Myr" means a mycarosyl group, represented by the structure below:

Myr = 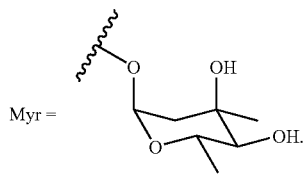

Where it is indicated that a group may be substituted, for example by use of "substituted or unsubstituted" or "optionally substituted" phrasing, such group may have one or more independently selected substituents, preferably one to five in number, more preferably one or two in number. It is understood that substituents and substitution patterns can be selected by one of ordinary skill in the art to provide compounds that are chemically stable and that can be synthesized by techniques known in the art as well as the methods set forth herein. Examples of suitable substituents include alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino quarternary ammonium, aralkylamino, cycloalkylamino, heterocycloamino, dialkylamino, alkanoylamino, thio, alkylthio, cycloalkylthio, heterocyclothio, ureido, nitro, cyano, carboxy, caroboxylalkyl, carbamyl, alkoxycarbonyl, alkylthiono, arylthiono, alkylsulfonyl, sulfonamindo, aryloxy, and the like, in addition to those specified herein. Where a different number and/or type of substituent(s) are specified in a particular context, such different specification prevails in respect of such particular context.

"Pharmaceutically acceptable salt" means a salt of a compound suitable for pharmaceutical formulation. Where a compound has one or more basic functionalities, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic moieties, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenyl-cyclohexylamine salt, benzathine salt, sodium salt, tetramethylammonium salt, and the like.

"Pharmaceutically acceptable ester" means an ester that hydrolyzes in vivo (for example in the human body) to produce the parent compound or a salt thereof or has per se activity similar to that of the parent compound. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include formates, acetates, propionates, butyrates, acrylates, citrates, succinates, and ethylsuccinates.

"Therapeutically effective amount" means that amount of active compound(s) or pharmaceutical agent(s) that elicit the biological or medicinal response in a tissue system, animal or human sought by a researcher, veterinarian, medical doctor or other clinician, which response includes alleviation of the symptoms of the disease or disorder being treated. The specific amount of active compound(s) or pharmaceutical agent(s) needed to elicit the biological or medicinal response will depend on a number of factors, including but not limited to the disease or disorder being treated, the active compound(s) or pharmaceutical agent(s) being administered, the method of administration, and the condition of the patient.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

The present invention includes within its scope prodrugs of the compounds of this invention. Such prodrugs are in general functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in Wermuth, "Designing Prodrugs and Bioprecursors," in Wermuth, ed., *The Practice of Medicinal Chemistry*, 2nd Ed., pp. 561-586 (Academic Press 2003).

Compounds and Methods

Turning now to preferred embodiments of compounds according to formula Ia (reproduced again below for convenience):

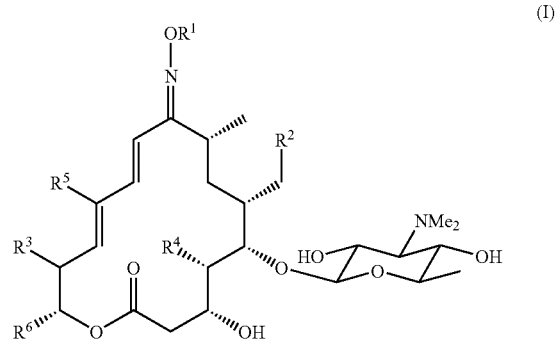

(I)

In the groups $R^1$, it is preferred that the length of the link ($C_1$-$C_5$ alkyl, $C_2$-$C_5$ alkenyl, $C_1$-$C_5$ alkyl-O—, etc.) between the groups Ar and the oxime oxygen be four atoms long, especially for compounds according to formula Ib or Ic. Preferred groups $R^1$ are

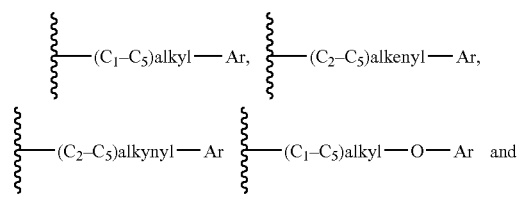

-continued

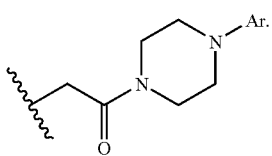

Where R² is

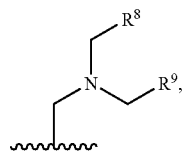

then R⁸ and R⁹ preferably combine to form (CH(CH₃)CH₂CH(CH₃)), corresponding to R² being

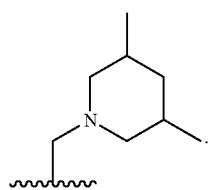

Where R³ is

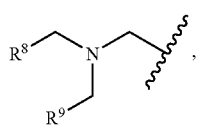

then R⁸ and R⁹ preferably are each H, corresponding to R³ being CH₂NMe₂.

Where a group Ar is substituted, the substituent preferably is halo, more preferably fluoro.

In one embodiment, Ar is other than unsubstituted or substituted phenyl, in particular when R¹ is

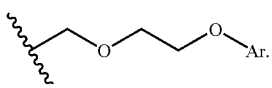

In another embodiment, R¹ is

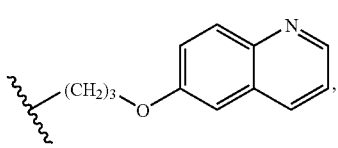

-continued

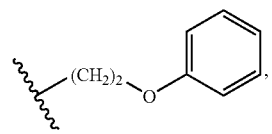

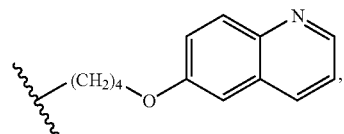

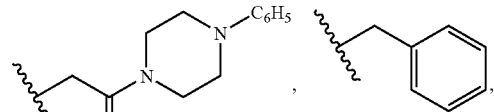

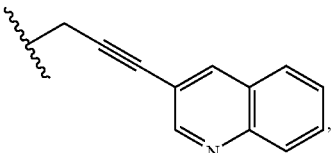

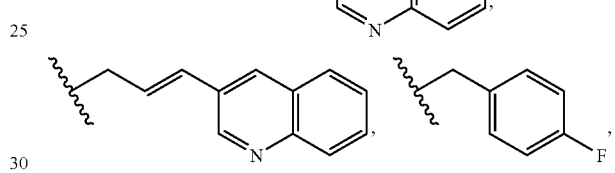

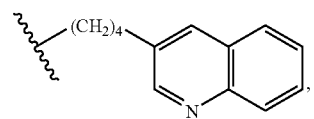, or

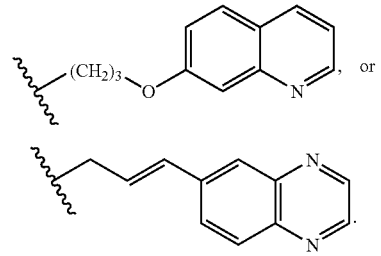

More preferably, R¹ is

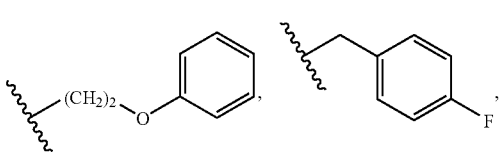

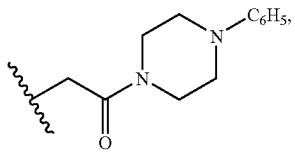

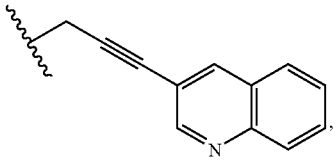

-continued

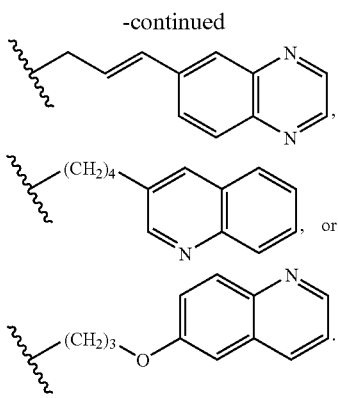

Most of the time, the Z-isomer of the $C_9$ oxime possess better activities than the corresponding E-isomers and are therefore preferred, although in some instances the potency pattern is reversed. However, compounds of this invention can be used as mixtures of the E and Z isomers, or as either isomer individually.

In a first preferred subgenus of compounds according to formula I, $R^4$ and $R^5$ are both Me and $R^6$ is Et, corresponding to a compound having a structure according to formula Ia:

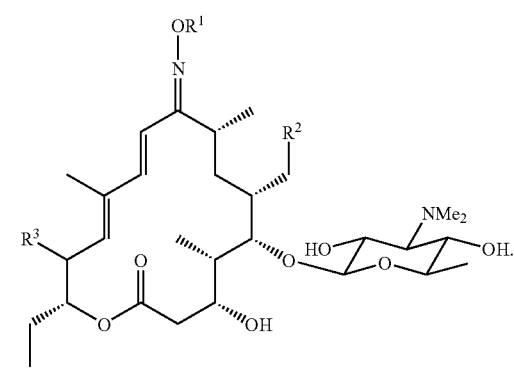

(Ia)

In a second preferred subgenus of compounds according to formula I, $R^2$ is CHO, $R^3$ is $CH_2OH$, $R^4$ and $R^5$ are both Me, and $R^6$ is Et, corresponding to a compound having a structure according to formula Ib:

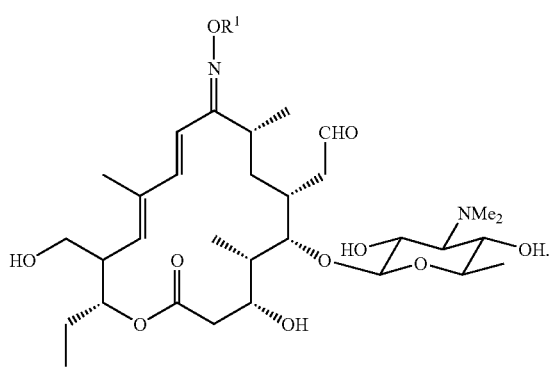

(Ib)

In one embodiment of compounds according to formula Ib, $R^1$ is selected from the group consisting of

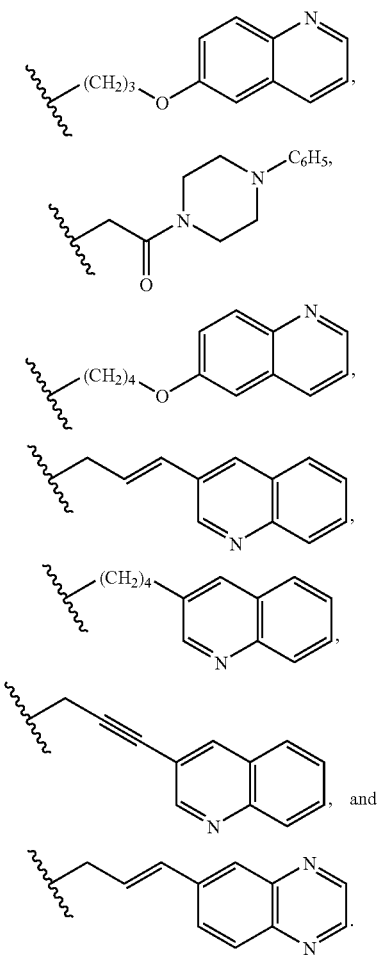

, and

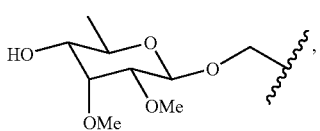

In a third preferred subgenus of compounds according to formula I, $R^2$ is

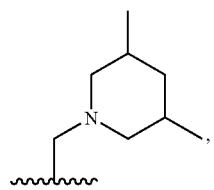

$R^3$ is

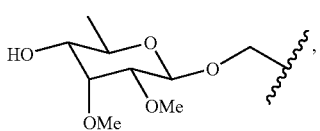

$R^4$ and $R^5$ are both Me, and $R^6$ is Et, corresponding to a compound having a structure according to formula Ic:

(Ic)

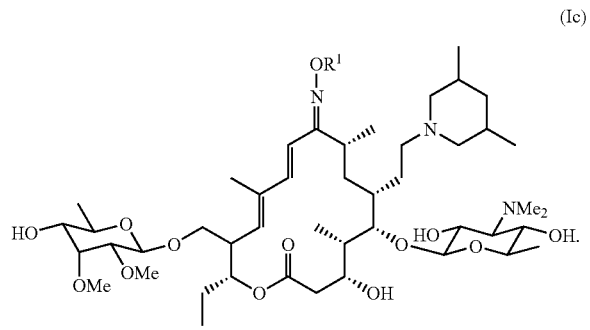

In one embodiment of compounds according to formula Ic, $R^1$ is other than H. Preferably, $R^1$ is selected from the group consisting of

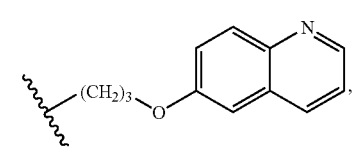

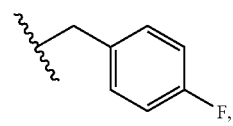

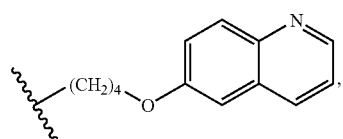

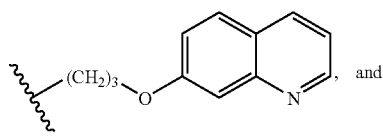, and

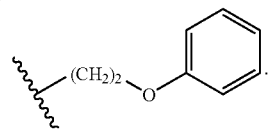.

In a fourth preferred subgenus of compounds according to formula I, $R^2$ is

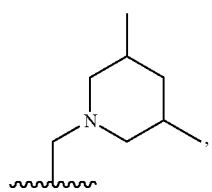, $R^3$ is $CH_2OH$, $R^4$ and $R^5$ are both Me, and $R^6$ is Et, corresponding to a compound having a structure according to formula Id:

(Id)

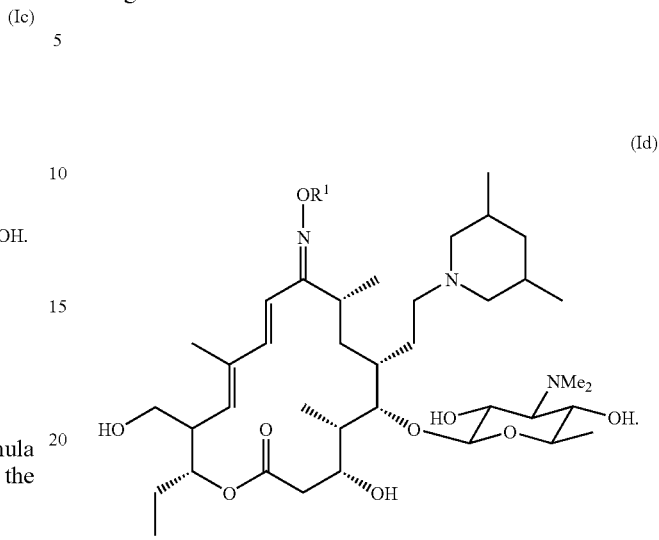

In one embodiment of compounds according to formula Id, $R^1$ is other than H. Preferably $R^1$ is selected from the group consisting of

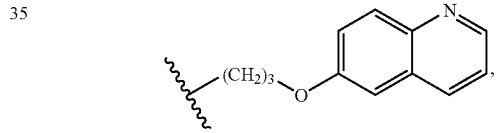

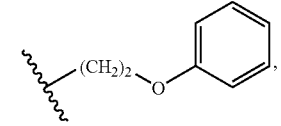

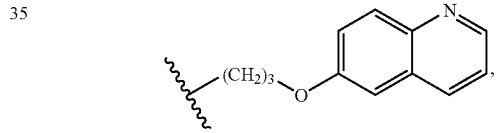

, and

.

In a fifth preferred subgenus of compounds according to formula I, $R^2$ is CHO, $R^3$ is $CH_2NMe_2$, $R^4$ and $R^5$ are both Me, and $R^6$ is Et, corresponding to a compound having a structure according to formula Ie:

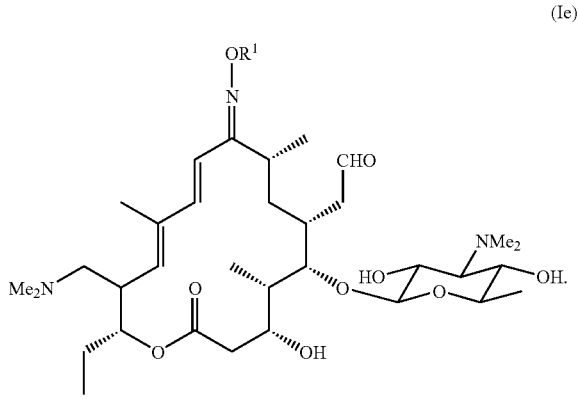

(Ie)

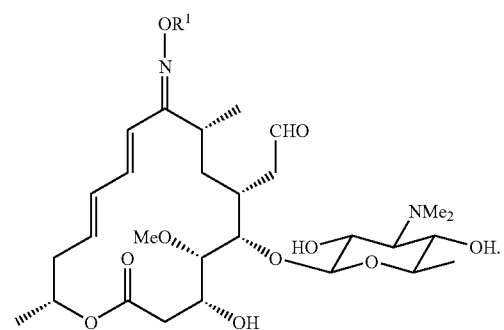

(Ig)

In a sixth preferred subgenus of compounds according to formula I, $R^2$ is CHO, $R^3$

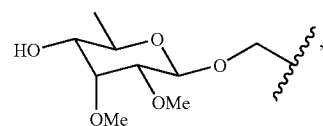

$R^4$ and $R^5$ are both Me, and $R^6$ is Et, corresponding to a compound having a structure according to formula If:

(If)

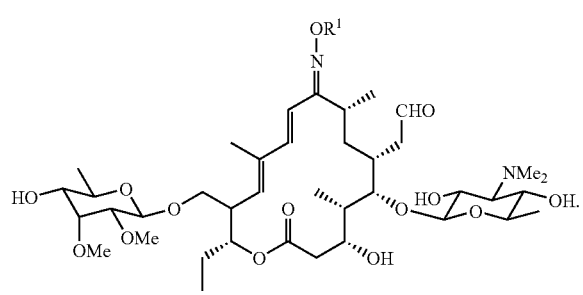

In a seventh preferred subgenus of compounds according to formula I, $R^2$ is CHO, $R^3$ is H, $R^4$ is OMe, $R^5$ is H, and $R^6$ is Me, corresponding to a compound having a structure according to formula Ig:

In an eighth preferred subgenus of compounds according to formula I, $R^2$ is CHO, $R^3$ is

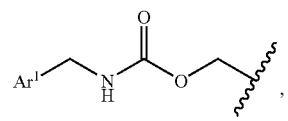

$R^4$ and $R^5$ are both Me, and $R^6$ is Et, corresponding to a compound having a structure according to formula Ih:

(Ih)

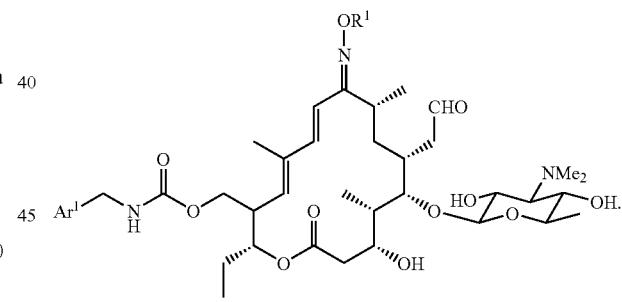

In one embodiment of compounds according to formula Ih, $Ar^1$ is phenyl. In another embodiment, $Ar^1$ is phenyl and $R^1$ is H. In another embodiment, $Ar^1$ is phenyl and $R^1$ is selected from the group consisting of

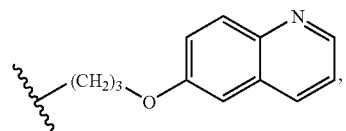

,

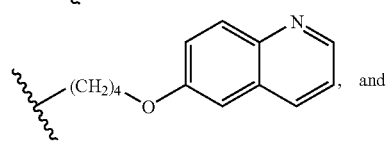

, and

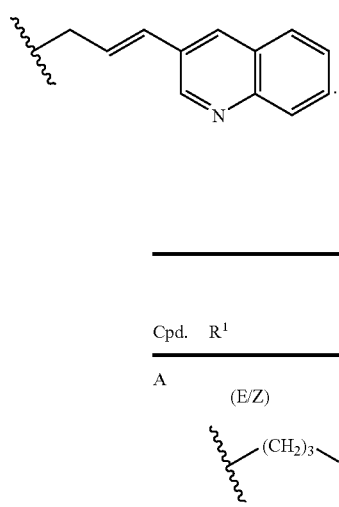

Exemplary compounds having a structure according to formula I are shown in Table A ($R^4$ and $R^5$ are both Me. $R^6$ is Et. The E/Z configuration of $OR^1$ in the oxime functionality is as noted adjacent to each $R^1$ group, with "E/Z" meaning a mixture of E and Z isomers.)

TABLE A

Exemplary Compounds

| Cpd. | $R^1$ | $R^2$ | $R^3$ |
|---|---|---|---|
| A | (E/Z) –(CH$_2$)$_3$–O–(6-quinolinyl) | CHO | CH$_2$OH |
| B | (Z) –(CH$_2$)$_4$–O–(6-quinolinyl) | Same | Same |
| C | (Z) –CH$_2$–C(O)–N(piperazinyl)–C$_6$H$_5$ | Same | Same |
| D | (E) –CH$_2$–C≡C–(3-quinolinyl) | Same | Same |
| E | (Z) –CH$_2$–C≡C–(3-quinolinyl) | Same | Same |
| F | (E) –CH$_2$–CH=CH–(3-quinolinyl) | Same | Same |
| G | (Z) –CH$_2$–CH=CH–(3-quinolinyl) | Same | Same |
| H | (Z) –CH$_2$–CH=CH–(6-quinoxalinyl) | Same | Same |

TABLE A-continued
Exemplary Compounds
| Cpd. | R¹ | R² | R³ |
|---|---|---|---|
| J | 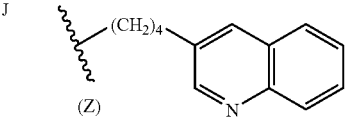 (Z) | Same | Same |
| K | 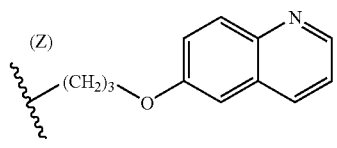 (Z) | 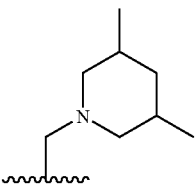 | 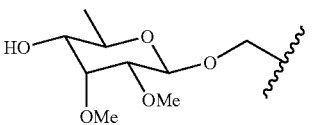 |
| L | 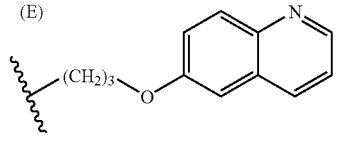 (E) | Same | Same |
| M | 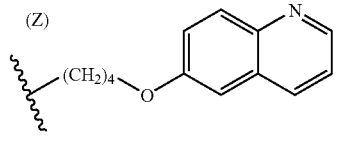 (Z) | Same | Same |
| N | 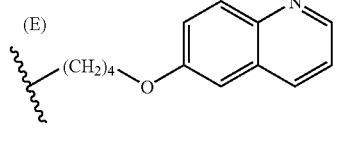 (E) | Same | Same |
| O | 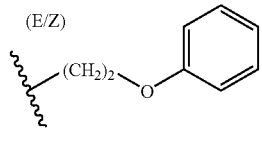 (E/Z) | Same | Same |
| P | 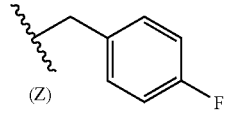 (Z) | Same | Same |
| Q | 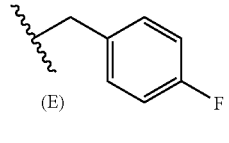 (E) | Same | Same |
| R | 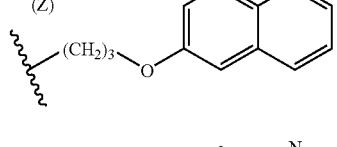 (Z) | Same | $CH_2OH$ |
| S | 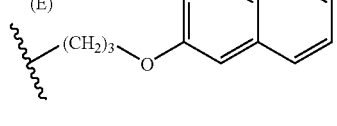 (E) | Same | Same |

TABLE A-continued

Exemplary Compounds

| Cpd. | R¹ | R² | R³ |
|---|---|---|---|
| T | 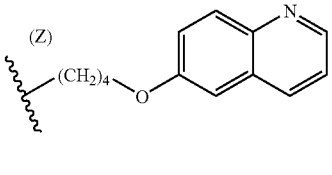 (Z), (CH₂)₄ linked to quinoline-O | 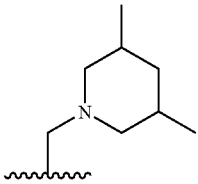 3,5-dimethylpiperidinyl-ethyl | CH₂OH |
| U | 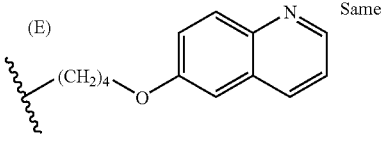 (E), (CH₂)₄-O-quinoline | Same | Same |
| V | 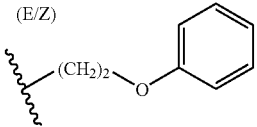 (E/Z), (CH₂)₂-O-phenyl | Same | Same |
| W | 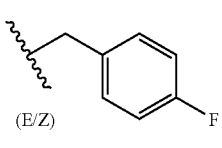 (E/Z), CH₂-(4-F-phenyl) | Same | Same |
| X | 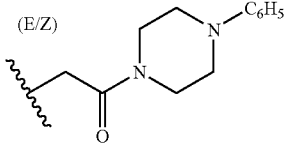 (E/Z), CH₂C(O)-N(piperazine)-N-C₆H₅ | Same | Same |
| Y | 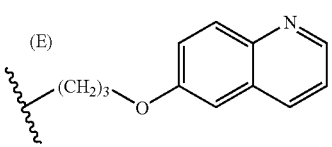 (E), (CH₂)₃-O-quinoline | CHO | CH₂NMe₂ |
| Z | 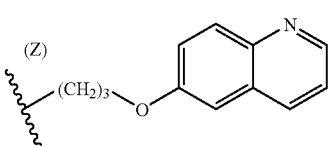 (Z), (CH₂)₃-O-quinoline | Same | Same |
| AA | 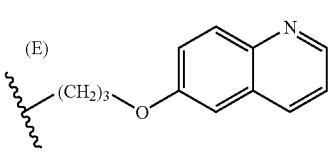 (E), (CH₂)₃-O-quinoline | CHO | 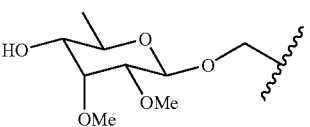 sugar with OMe, OMe, OH |
| BB | 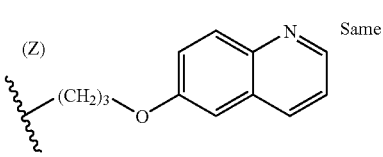 (Z), (CH₂)₃-O-quinoline | Same | Same |

TABLE A-continued

Exemplary Compounds

| Cpd. | R¹ | R² | R³ |
|---|---|---|---|
| CC | (E) 7-quinolinyl-O-(CH₂)₃- | 3,5-dimethylpiperidinyl-ethyl | HO, OMe, OMe sugar |
| DD | (E/Z) 6-quinolinyl-O-(CH₂)₃- | CHO | benzyl-NH-C(O)-O- |
| EE | (E/Z) 6-quinolinyl-O-(CH₂)₄- | Same | Same |
| FF | (E/Z) 3-quinolinyl-CH=CH-CH₂- | Same | Same |
| GG | (E/Z) H | Same | Same |

An example of a compound having a structure according to formula Ig is compound HH, shown below:

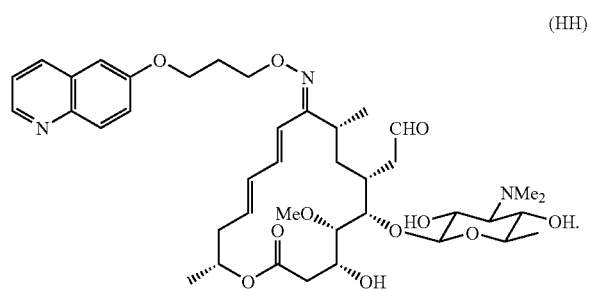

(HH)

FIG. 1 shows schematically the methodology employed for the synthesis of compounds Ib. The starting material was 5-O-mycaminosyltylonolide (1, "OMT," Gorman et al., U.S. Pat. No. 3,459,853 (1969), incorporated herein by reference). The C-19 aldehyde group of OMT was protected as the 1,3-dioxolane by treatment with ethylene glycol in the presence of camphorsulfonic acid ("CSA") in $CH_2Cl_2$, to produce 1,3-dioxolane 2. Conversion of the C-9 ketone group of 1,3-dioxolane 2 to the oxime was carried out using $NH_2OH \cdot HCl$ in the presence of pyridine, yielding oxime 3. Oxime 3 was then converted to alkylated oxime 4 by selective alkylation on the C-9 oxime oxygen using an arylalkyl bromide R¹Br and KOtBu in DMF. In many cases, E and Z oximes could be separated by reverse phase high pressure liquid chromatography ("HPLC"). Finally, compound Ib was obtained by de-protection of the C-19 aldehyde was achieved by stirring alkylated oxime 4 in acetone and CSA.

Figure 2:
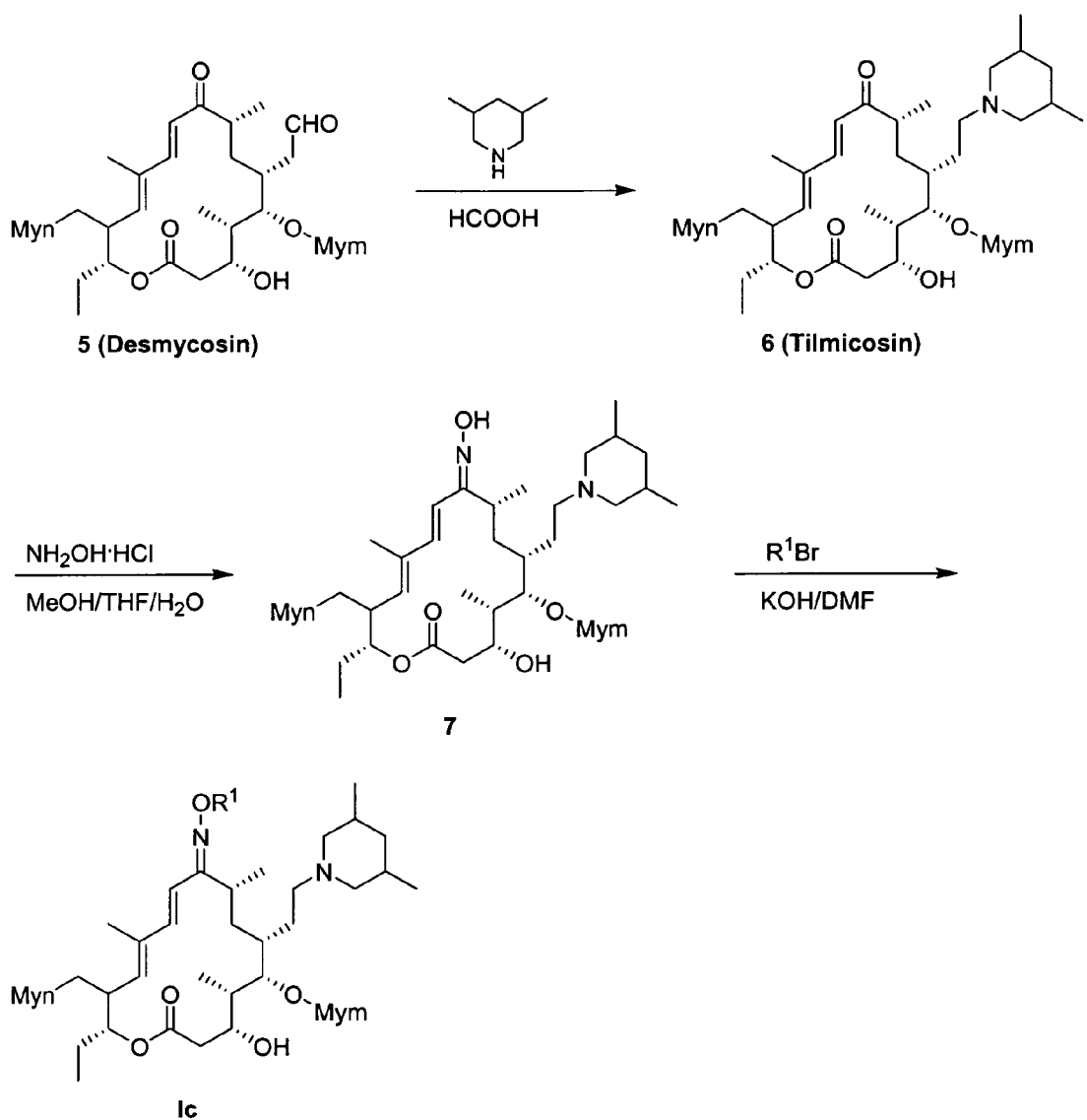

FIG. 2 shows schematically the synthesis of compounds Ic. Tilmicosin (6) was prepared from desmycosin (5) via reductive amination using 3,5-dimethylpiperidine in the presence of formic acid (Debono et al., J. Antibiot. 42 (8), 1253-1267 (1989), incorporated herein by reference). Tilmicosin 9-oxime 7 was obtained by oximation of tilmicosin 6 with $NH_2OH \cdot HCl$ in MeOH-THF-$H_2O$. Alkylation of tilmicosin 9-oxime 7 with an arylalkyl bromide R¹Br gave compound Ic.

Figure 3:
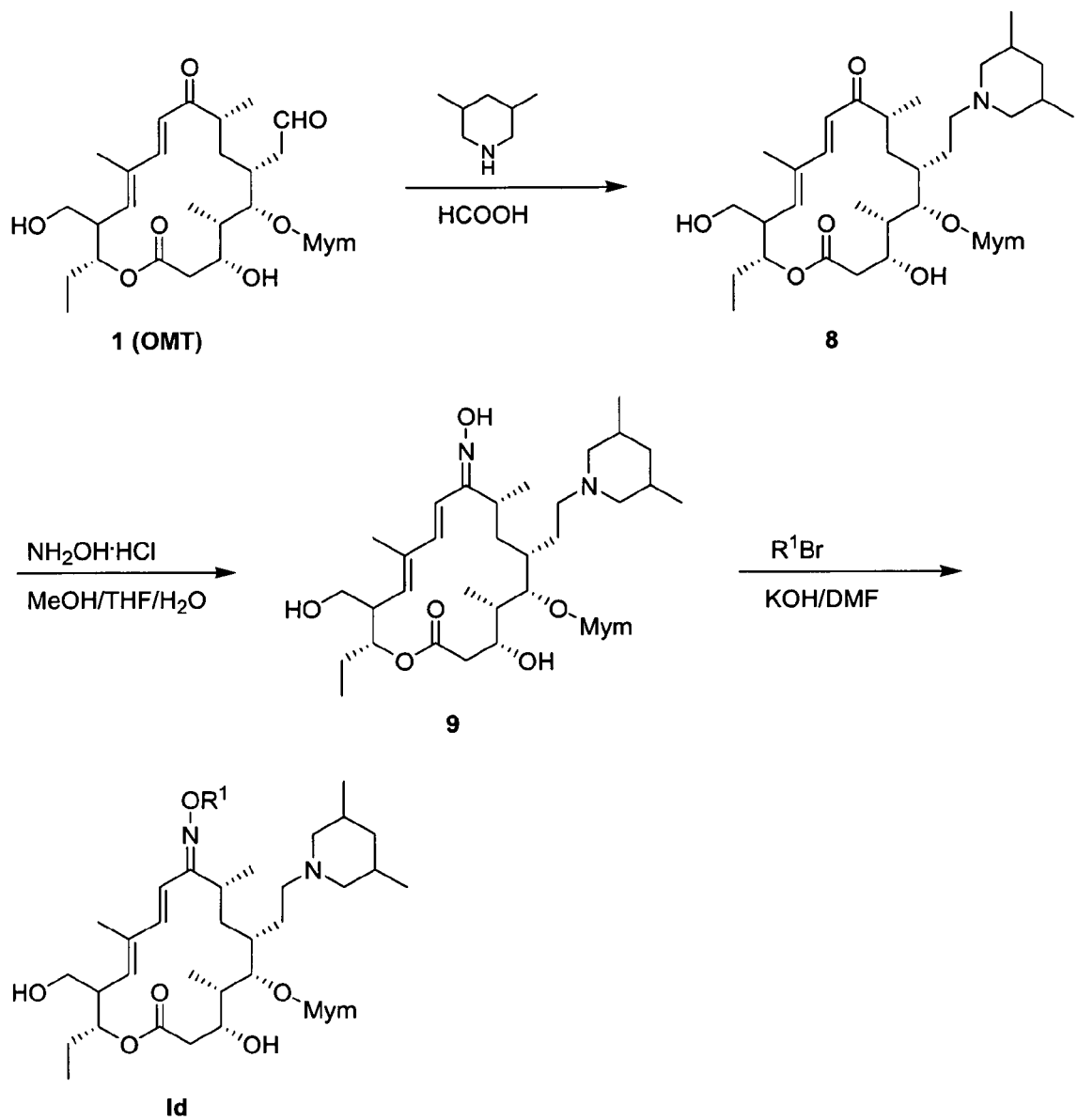

Compounds according to formula Id can be made by the scheme shown in FIG. 3. 20-Deoxy(3,5,-dimethyl-1-piperidine)OMT (8, "DDP-OMT") was prepared from OMT 1 by reductive amination generally as described in the context of FIG. 2. DDP-OMT 8 was then oximated to give oxime 9, which was in turn alkylated to give compound Id.

Figure 4:
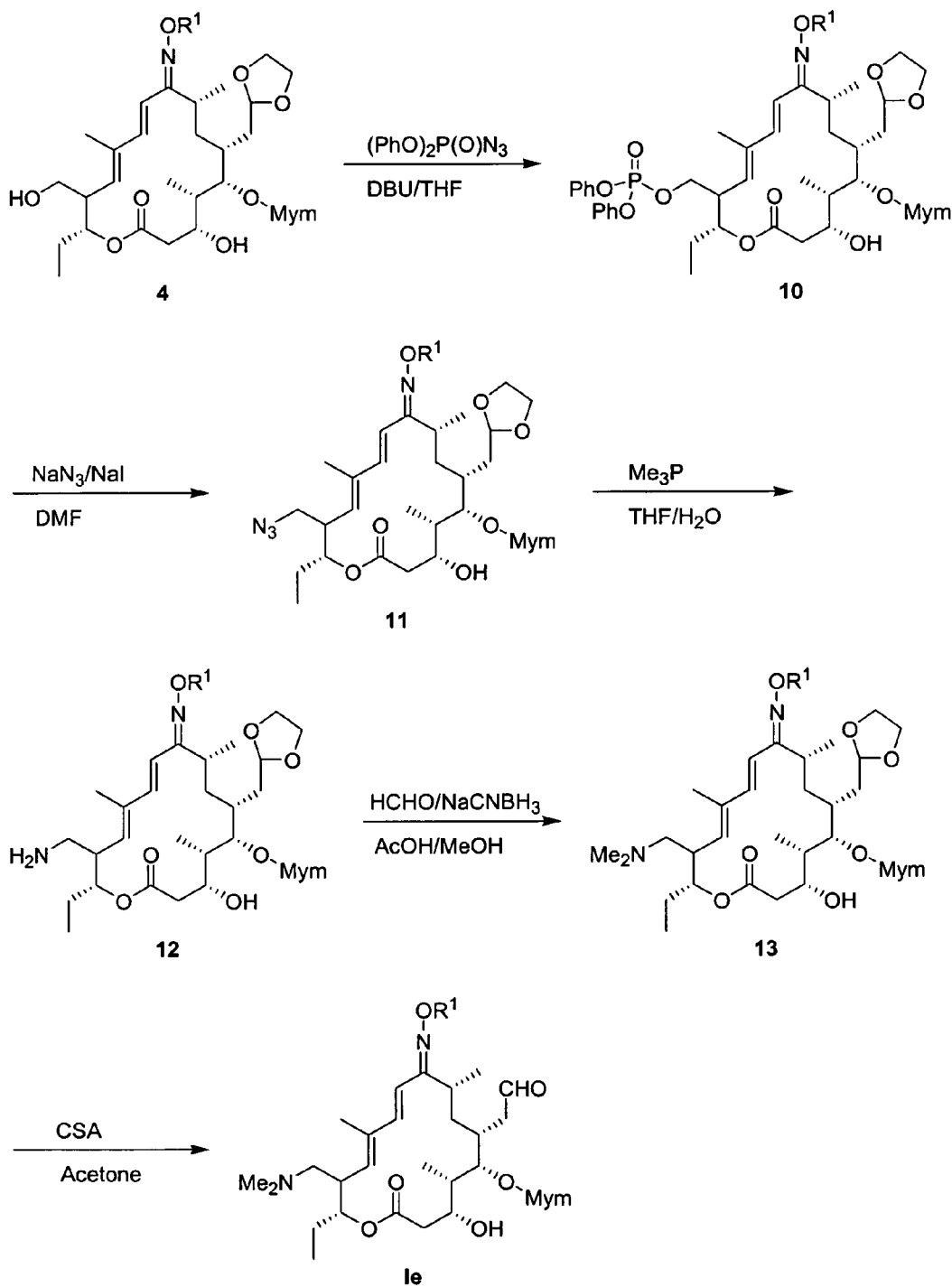

FIG. 4 shows schematically the synthetic methodology for making compounds Ie. Alkylated oxime 4 (FIG. 1) was converted to phosphate ester 10 by reacting with diphenylphosphoryl azide ("DPPA"). Phosphate ester 10 was then converted to 23-azido compound 11 by heating in the presence of $NaN_3$ and a catalytic amount of NaI in DMF. 23-Azido compound 11 was reduced to amine 12 with $Me_3P$. Reductive alkylation of amine 12 with $NaCNBH_3$ in acetic acid-formaldehyde gave dimethylamine 13. Lastly, deprotection of the C-19 aldehyde with CSA-acetone converted dimethylamine 13 to compound Ie. The E- and Z-isomers could be separated by HPLC.

Compounds having the structures of formulae If and Ig were prepared starting from desmycomysin 5 and compound 14, respectively, using a sequence of reactions analogous to that shown in FIG. 1.

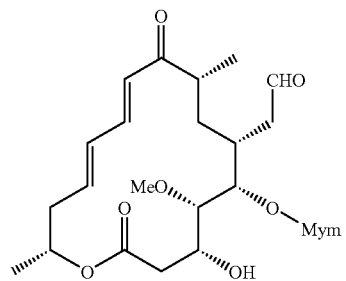

14

Compounds of this invention can be used to treat infections by Gram-positive or Gram-negative bacteria, in particular infections by *Streptococcus pneumoniae, Staphylococcus aureus, Staphylococcus epidermidis, Haemophilus influenzae,* and *Enterococcus faecalis.*

Preferably, compounds of this invention are provided in a purified and isolated form, for example following column chromatography, high-pressure liquid chromatography, recrystallization, or other purification technique. Where particular stereoisomers of compounds of this invention are specified, such stereoisomers preferably are substantially free of other stereoisomers.

Compounds of this invention may be used in a pharmaceutical formulation comprising a compound of this invention and an excipient. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy,* 20th Ed. (Lippincott Williams & Wilkins 2003), the disclosure of which is incorporated herein by reference.

For human administration, an effective amount of a compound of this invention is used, optionally in combination with a pharmaceutically acceptable carrier. Generally, an effective amount is a dose of 200 to 500 mg daily for an adult. The composition may be dry, or it may be a solution. Treatment may be reactive, for treating an existing condition, or prophylactic, to forestall development of a condition. Compounds of this invention can be used in the preparation of a medicament. The compounds may be administered orally, topically, or parenterally (e.g., intravenously, subcutaneously, intraperitoneally, transdermally). Compounds of this invention can also be used in veterinary applications, especially for the treatment of non-human mammals.

The practice of this invention can be further understood by reference to the following examples, which are provided by way of illustration and not of limitation.

EXAMPLE 1

Compounds Ib

This example describes the preparation of compounds according to formula Ib, using compound D as the archetype and following the scheme of FIG. 1.

Step 1: 1.3-Dioxolane 2. CSA (93 mg, 0.4008 mmol, 1.5 eq) and $HOCH_2CH_2OH$ (166 mg, 10 eq) were added to a solution of OMT (160 mg, 0.2676 mmol) in $CH_2Cl_2$ (0.5 mL). The reaction mixture was stirred at room temperature ("RT") overnight. $CHCl_3$ (50 mL) was added to the reaction mixture. The organic phase was washed with saturated $NaHCO_3$ (3×20 mL), dried over $Na_2SO_4$, filtered, and evaporated to dryness. The product was purified on silica gel column (1%-3% MeOH in $CH_2Cl_2$ with 1% $Et_3N$) to obtain 120 mg of 1,3-dioxolane 2.

Step 2: Oxime 3. $NH_2OH.HCl$ (10 eq) and pyridine (10 eq) were added to 1,3-dioxolane 2 (60 mg, 0.09346 mmol) dissolved in MeOH (3 mL). The reaction mixture was stirred at RT overnight. $CHCl_3$ (50 mL) was added to the reaction mixture. The organic phase was washed with saturated $NaHCO_3$ (3×20 mL), dried over $Na_2SO_4$, filtered, and evaporated to dryness to give oxime 3 (50 mg) as a mixture of E- and Z-isomers. Oxime 3 was used without purification in the next step.

Step 3: Alkylated oxime 4. Oxime 3 (53 mg, 0.06401 mmol) and 6-(3-bromo-prop-1-ynyl)quinoline (1.5 eq) were placed in a 5 mL round bottom flask, which was then flushed with nitrogen. Freshly distilled THF (2 mL) and dry DMF (0.4 mL) were added at RT. KOtBu (96 μL, 1M in THF) was added and the reaction mixture was stirred at RT for 2 hr. $CHCl_3$ (50 mL) was added. The organic phase was washed with saturated $NaHCO_3$ (3×20 mL), dried over $Na_2SO_4$, filtered, and evaporated to dryness. The product was subjected to HPLC purification (C18-reverse phase column, solvent A: $H_2O$ with 5 mM $NH_4OAc$, solvent B: $CH_3CN$/MeOH (4/1) with 5 mM $NH_4OAc$, 50%-55% B over 25 minutes) to obtain 11 mg of the alkylated Z oxime 4 and 8.9 mg of the alkylated E oxime 4.

Step 4: Compound D. Alkylated E oxime 4 (20 mg), CSA (10 mg), and acetone (1 mL) were stirred at RT for 2 days. The acetone was removed. The product was purified by silica gel column ($CH_2Cl_2$ with 1% $Et_3N$ to 1-3% MeOH in $CH_2Cl_2$ with 1% $Et_3N$) to obtain 15 mg of compound D. $^1H$ NMR (400 MHz, $CDCl_3$) δ (ppm) 9.71 (s, 1H), 8.91 (d, J=2 Hz, 1H), 8.29 (s, 1H), 8.07 (d, J=8.4 Hz, 1H), 7.81 (d, J=7.2 Hz, 1H), 7.71 (dd, J=8.4 Hz, 8.4 Hz, 1H), 7.56 (dd, J=8 Hz, 8 Hz, 1H), 7.00 (d, J=15.6 Hz, 1H), 5.91 (d, J=15.6 Hz, 1H), 5.58 (d, J=10.4 Hz, 1H), 4.93 (m, 3H), 4.30 (m, 1H), 4.24 (d, J=7.6 Hz, 1H), 3.91 (m 1H), 3.66 (dd, J=7.2 Hz, 10.4 Hz, 1H), 3.49 (dd, J=7.2 Hz, 10.4 Hz 1H), 3.24 (m, 1H), 3.04 (dd, J=9.6 Hz, 9.6 Hz, 1H), 2.97 (dd, J=10.8 Hz, 17.6 Hz, 1H), 2.85 (m, 1H), 2.51 (s, 6H), 1.79 (s, 3H), 1.23 (d, J=6.0 Hz, 3H), 1.15 (d, J=6.8 Hz, 3H), 1.00 (d, J=6.4 Hz, 3H), 0.94 (t, J=7.2, 3H), LC-MS (m/z) calculated for $C_{43}H_{59}N_3O_{10}$ 777.42. found 778.79 (M+1).

Other compounds Ib were prepared following the above procedure, mutatis mutandis. In some instances as noted, the E/Z oxime isomers were not separated.

Compound A. The E/Z oximes (E:Z ratio 1.5:1 by $^1H$ NMR) were not separated in step 3. $^1H$ NMR (400 MHz, $CDCl_3$) δ (ppm) 9.72 (s, 1H, Z), 9.67 (s, 1H, E), 8.74 (dd, J=1.6 Hz, 5.2 Hz, 1H, E+Z), 8.09 (d, J=8.4 Hz, 1H, E+Z), 8.00 (d, J=9.2 Hz, 1H, E+Z), 7.42 (dd, J=2.74 Hz, 9.4 Hz, 1H, E), 7.34 (dd, J=4.3 Hz, 8.4 Hz, 1H, E+Z), 7.14 (d, J=2.74 Hz, 1H, Z), 7.12 (d, J=2.74 Hz, 1H, E), 6.75 (d, J=15.5 Hz, 1H, E), 5.87 (d, J=15.5 Hz, 1H, E), 5.38 (d, J=10.4 Hz, 1H, E), 5.38 (d, J=10.4 Hz, 1H, E), 5.30 (d, J=10.4 Hz, 1H, Z), 4.86 (dt, J=2.0 Hz, 9.8 Hz, 1H, E), 4.77 (m, 1H, Z), 2.50 (s, 6H, Z), 2.49 (s, 6H, E), 1.76 (s, 3H, Z), 1.74 (s, 3H, E), LC-MS (m/z) calculated for $C_{43}H_{63}N_3O_{11}$ 797.45. found 798.66 (M+1).

Compound B. $^1$H NMR (400 MHz, CDCl$_3$) δ (ppm) 9.70 (s, 1H), 8.74 (s, 1H), 8.03 (d, J=7.2 Hz, 1H), 7.96 (d, J=9.2 Hz, 1H), 7.72 (br, 1H), 7.52 (dd, 1H), 7.07 (d, J=2.4 Hz, 1H), 4.92 (dt, J=2.74 Hz, 9.78 Hz, 1H), 4.32 (d, J=7.2 Hz, 1H), 3.05 (dd, J=9.2 Hz, 9.2 Hz, 1H), LC-MS (m/z) calculated for C$_{44}$H$_{65}$N$_3$O$_{11}$ 811.46. found 813.0 (M+1).

Compound C. $^1$H NMR (400 MHz, CDCl$_3$) δ (ppm) 9.70 (s, 1H), 7.27 (m, 2H), 6.91 (m, 3H), 5.52 (d, J=10 Hz, 1H), 4.93 (dt, J=2.54 Hz, 9.4 Hz, 1H), 4.74 (d, J=13.8 Hz, 1H), 4.31 (d, J=7.2 Hz, 1H), 3.89-3.60 (m, 8H), 3.52 (dd, J=7.6 Hz, 10 Hz, 1H), 3.29 (m, 1H), 3.16 (br, 3H), 3.03 (dd, J=9.2 Hz, 9.2 Hz, 1H), 2.87 (m, 2H), 2.60 (m, 1H), 2.50 (s, 6H), 2.36 (m, 2H), 1.97 (d, J=16.4 Hz, 1H), 1.80 (s, 3H), 1.61 (m, 2H), 1.41 (m, 2H), 1.26 (d, J=6.3 Hz, 3H), 1.19 (d, J=6.65 Hz, 3H), 0.98 (d, J=7.0 Hz, 3H), 0.94 (t, J=7.0, 3H), LC-MS (m/z) calculated for C$_{43}$H$_{66}$N$_4$O$_{11}$ 814.47. found 816.0 (M+1).

Compound E. $^1$H NMR (400 MHz, CDCl$_3$) δ (ppm) 9.69 (s, 1H), 8.87 (d, J=2 Hz, 1H), 8.26 (d, J=1.6 Hz, 1H), 8.08 (d, J=8.4 Hz, 1H), 7.80 (d, J=7.2 Hz, 1H), 7.71 (dd, J=8.8 Hz, 8.8 Hz, 1H), 7.56 (dd, J=8 Hz, 8 Hz 1H), 5.70 (br, 1H), 4.89-4.98 (m, 3H), 4.30 (d, J=7.2 Hz, 1H), 3.88 (d, J=10.4 Hz, 1H), 3.64-3.83 (m, 3H), 3.54 (dd, J=7.4 Hz, 10.2 Hz, 1H), 3.28 (m, 1H), 3.02 (dd, J=9.2 Hz, 9.2 Hz, 1H), 2.89 (m, 1H), 2.49 (s, 6H), 1.82 (s, 3H), 1.62 (m, 2H), 1.25 (d, J=7.2 Hz, 3H), 1.23 (d, J=8 Hz, 3H), 0.99 (d, J=6.4 Hz, 3H), 0.94 (t, J=8.8, 3H), LC-MS (m/z) calculated for C$_{43}$H$_{59}$N$_3$O$_{10}$ 777.42. found 778.75 (M+1).

Compound F. $^1$H NMR (400 MHz, CDCl$_3$) δ (ppm) 9.70 (s, 1H), 8.96 (d, J=2 Hz, 1H), 8.10 (s, 1H), 8.05 (d, J=8.4 Hz, 1H), 7.81 (d, J=8.4 Hz, 1H), 7.66 (dd, J=7.2 Hz, 7.2 Hz, 1H), 7.52 (dd, J=6.8 Hz, 6.8 Hz 1H), 6.94 (d, J=15.6 Hz, 1H), 6.72 (d, J=16.2 Hz, 1H), 6.54 (dt, J=5.9 Hz, 16.0 Hz, 1H), 5.88 (d, J=15.6 Hz,1H), 5.54 (d, J=10.8 Hz, 1H), 4.89 (dt, J=11.9 Hz, 2.4 Hz, 1H), 4.24 (d, J=7.6 Hz, 1H), 3.92 (d, J=10.8 Hz, 1H), 3.63-3.76 (m, 3H), 3.48 (dd, J=7.6 Hz, 10.4 Hz, 1H), 3.22 (m, 1H), 3.04 (dd, J=9.6 Hz, 9.6 Hz, 1H), 2.86 (m, 1H), 2.48 (s, 6H), 1.77 (s, 3H), 1.60 (m, 1H), 1.42 (m, 1H), 1.22 (d, J=6.0 Hz, 3H), 1.14 (d, J=6.8 Hz, 3H), 1.01 (d, J=6.8 Hz, 3H), 0.92 (t, J=7.2 Hz, 3H), LC-MS (m/z) calculated for C$_{43}$H$_{61}$N$_3$O$_{10}$ 779.44. found 780.66 (M+1).

Compound G. $^1$H NMR (400 MHz, CDCl$_3$) δ (ppm) 9.68 (s, 1H), 8.93 (d, J=2.4 Hz, 1H), 8.11 (s, 1H), 8.04 (d, J=8.4 Hz, 1H), 7.81 (d, J=7.4 Hz, 1H), 7.66 (dd, J=6.4 Hz, 7.0 Hz, 1H), 7.52 (dd, J=7.0 Hz, 7.0 Hz 1H), 6.73 (d, J=16.4 Hz, 1H), 6.57 (dt, J=16.0 Hz, 5.3 Hz, 1H), 5.58 (d, J=8.0 Hz,1H), 4.94 (m, 1H), 4.78 (d, J=5.2 Hz, 1H), 4.30 (d, J=7.2 Hz, 1H), 3.89 (d, J=10.0 Hz, 1H), 3.65-3.75 (m, 3H), 3.53 (dd, J=7.2 Hz, 10.6 Hz, 1H), 3.28 (m, 1H), 3.03 (dd, J=9.6 Hz, 9.6 Hz, 1H), 2.90 (m, 1H), 2.49 (s, 6H), 1.82 (s, 3H), 1.61 (m, 1H), 1.20 (d, J=6.8 Hz, 3H), 0.99 (d, J=6.4 Hz, 3H), 0.93 (t, J=7.2, 3H), LC-MS (m/z) calculated for C$_{43}$H$_{61}$N$_3$O$_{10}$ 779.44. found 780.68 (M+1).

Compound H. $^1$H NMR (400 MHz, CDCl$_3$) δ (ppm) 9.71 (s, 1H), 8.80 (s, 1H), 8.77 (dd, J=11.5 Hz, 13.5 Hz, 1H), 8.06 (d, J=9.2 Hz, 1H), 8.00 (d, J=7.0 Hz, 1H), 7.97 (d, J=5.3 Hz, 1H), 6.91 (d, J=15.9 Hz, 1H), 6.58 (dt, J=16.2 Hz, 4.5 Hz, 1H), 5.53 (d, J=11.4 Hz,1H), 5.0 (dt, J=10.2 Hz, 2.9 Hz, 1H), 4.77-4.88 (m, 2H), 4.25 (d, J=7.4 Hz, 1H), 3.90 (d, J=10.4 Hz, 1H), 3.75-3.85 (m, 3H), 3.52 (dd, J=8.4 Hz, 10.4 Hz, 1H), 3.26 (m, 1H), 3.07 (dd, J=7.6 Hz, 10.0 Hz, 1H), 2.93 (m, 1H), 2.52 (s, 6H), 1.86 (s, 3H), 1.65 (m, 1H), 1.22 (d, J=6.9 Hz, 3H), 1.00 (d, J=6.9 Hz, 3H), 0.96 (t, J=7.2 Hz, 3H), LC-MS (m/z) calculated for C$_{42}$H$_{60}$N$_4$O$_{10}$ 780.43. found 781.70 (M+1).

Compound J. $^1$H NMR (400 MHz, CDCl$_3$) δ (ppm) 9.70 (s, 1H), 8.75 (d, J=1.6 Hz, 1H), 8.08 (d, J=8.4 Hz, 1H), 7.94 (s, 1H), 7.78 (d, J=7.6 Hz, 1H), 7.66 (dd, J=8.0 Hz, 8.0 Hz, 1H), 7.54 (dd, J=7.2 Hz, 7.2 Hz, 1H), 5.72 (d, J=10 Hz, 1H), 5.07 (m, 1H), 4.29 (d, J=7.43 Hz, 1H), 3.51(dd, J=7.6 Hz, 10.4 Hz, 1H), 3.27 (m, 1H), 3.04 (dd, J=9.2 Hz, 9.2 Hz, 1H), 2.50 (s, 6H), 1.80 (s, 3H), 1.28 (d, J=6.5 Hz, 3H), 1.17 (d, J=6.8 Hz, 3H), 1.00 (d, J=6.8 Hz, 3H), 0.98 (t, J=7.8, 3H), LC-MS (m/z) calculated for C$_{44}$H$_{65}$N$_3$O$_{10}$ 795.47. found 796.66 (M+1).

Compound IIa. $^1$H NMR (400 MHz, CDCl$_3$) δ (ppm) 9.66 (s, 1H), 7.29 (d, J=8.4 Hz, 2H), 6.94 (m, 3H), 5.43 (d, J=8.4 Hz, 1H), 4.93 (dt, J=9.4 Hz, 2.5 Hz, 1H), 4.37 (m, 2H), 4.3(d, J=7.2 Hz, 1H), 4.19 (m, 2H), 3.82 (m, 2H), 3.69 (dd, J=4.7 Hz, 10.7 Hz, 1H), 3.62 (dd, J=6.85 Hz, 11.5 Hz, 1H), 3.52 (dd, J=7.6 Hz, 11.0 Hz, 1H), 3.30 (m, 1H), 3.02 (dd, J=9.8 Hz, 9.8 Hz, 1H), 2.87 (m, 1H), 2.49 (s, 6H), 2.35 (dd, J=9.6 Hz, 9.6 Hz, 1H), 1.97 (d, J=16.0 Hz, 1H), 1.83 (m, 1H), 1.79(s, 3H), 1.60 (m, 2H), 1.28 (d, J=6.0 Hz, 3H), 1.19 (d, J=6.8 Hz, 3H), 0.97 (d, J=7.2 Hz, 3H), 0.94 (t, J=7.2, 3H), LC-MS (m/z) calculated for C$_{39}$H$_{60}$N$_2$O$_{11}$ 732.42. found 734.0 (M+1).

Compound IIb. $^1$H NMR (400 MHz, CDCl$_3$) δ (ppm) 9.67 (s, 1H), 7.29 (d, 1H), 6.95 (d, 1H), 5.89 (d, J=15.6 Hz, 1H), 5.53 (d, J=10.4 Hz, 1H), 4.91 (dt, 1H), 4.39(dd, J=4.4 Hz, 4.4 Hz, 1H), 3.93 (d, J=10.4 Hz, 1H), 3.49 (dd, J=7.6 Hz, 10.8 Hz, 1H), 3.24 (dd, J=6.0 Hz, 8.8 Hz, 1H), 3.06 (dd, J=9.2 Hz, 9.2 Hz, 1H), 3.30 (m, 1H), 3.02 (dd, J=9.8 Hz, 9.8 Hz, 1H), 2.52 (s, 6H), 1.10 (d, J=6.8 Hz, 3H), 0.99 (d, J=6.8 Hz, 3H), 0.95 (t, J=7.6, 3H), LC-MS (m/z) calculated for C$_{39}$H$_{60}$N$_2$O$_{11}$ 732.42. found 734.0 (M+1).

Compound IIc. $^1$H NMR (400 MHz, CDCl$_3$) δ (ppm) 9.61 (s, 1H), 6.92 (d, J=15.6 Hz, 1H), 5.89 (d, J=15.6 Hz, 1H), 5.53 (d, J=10.4 Hz, 1H), 4.91 (dt, J=9.6 Hz, 2.7 Hz, 1H), 4.24(dd, J=7.4 Hz, 1H), 3.93 (d, J=10.2 Hz, 1H), 3.48 (dd, J=7.4 Hz, 10.4 Hz, 1H), 3.23 (dd, J=5.9 Hz, 8.6 Hz, 1H), 3.03 (dd, J=9.4 Hz, 9.4 Hz, 1H), 2.50 (s, 6H), 1.79 (s, 3H), 1.10 (d, J=6.8 Hz, 3H), 1.00 (d, J=6.8 Hz, 3H), 0.95 (t, J=7.6, 3H), LC-MS (m/z) calculated for C$_{38}$H$_{57}$FN$_2$O$_{10}$ 720.40. found 722.0 (M+1).

Compound IId. $^1$H NMR (400 MHz, CDCL$_3$) δ (ppm) 9.63 (s, 1H), 7.30 (dd, J=5.9 Hz, 8.4 Hz, 2H), 7.02 (dd, J=8.6 Hz, 8.6 Hz, 1H), 6.02 (s, br, 1H), 5.46 (d, J=10.4 Hz, 1H), 5.04 (m, 2H), 4.93 (m, 1H), 4.30 (dd, J=724 Hz, 1H), 3.86 (d, J=3.9 Hz, 1H), 3.81 (m, 1H), 3.71 (dd, J=4.1 Hz, 10.8 Hz, 1H), 3.64 (dd, J=6.9 Hz, 6.9 Hz, 1H), 3.52 (dd, J=8.0, Hz, 10.2 Hz, 1H), 3.30 (m, 1H), 3.03 (dd, J=9.1 Hz, 9.1 Hz, 1H), 2.87 (m, 1H), 2.83 (dd, J=8.0 Hz, 18.0 Hz, 1H), 2.60 (m, 1H), 2.49 (s, 6H), 2.36 (dd, J=10.2 Hz, 10.2 Hz, 1H), 2.23 (m, 1H), 1.98 (d, J=15.9 Hz, 1H), 1.80 (s, 3H), 1.59 (m, 2H), 1.28 (d, J=6.3 Hz, 3H), 1.18 (d, J=6.6 Hz, 3H), 0.97 (d, J=7.0 Hz, 3H), 0.94 (t, J=7.2 Hz, 3H), LC-MS (m/z) calculated for C$_{38}$H$_{57}$FN$_2$O$_{10}$. found 722.0 (M+1).

EXAMPLE 2

Compounds Ic

This example describes the preparation of compounds according to formula Ic, using compounds K and L as the archetypes and following the scheme in FIG. 2.

Step 1: Tilmicosin 9-oxime 7. Tilmicosin (6, 0.5754 mmol; Debono et al., *J. Antibiot.* 42 (8), 1253-1267 (1989), incorporated herein by reference) was dissolved in MeOH (24 mL), THF (6 mL), and H$_2$O (2 mL). NH$_2$OH.HCl (0.8 g, 11.5 mmol) was added. The reaction mixture was heated to 50° C. for 5 hr. The MeOH and THF were removed under reduced pressure. EtOAc (200 mL) was added. The organic phase was washed with saturated NaHCO$_3$ (3×100 mL), dried over Na$_2$SO$_4$, filtered, and evaporated to dryness to give tilmiconsin 9-oxime 7 (234 mg) as a mixture of E and Z isomer, which was used in the next step without purification.

Step 2: Compounds K and L. To a solution of tilmicosin 9-oxime 7 (60 mg, 0.06787 mmol) in DMF (0.5 mL) was added 6-(3-bromo-propoxy)quinoline (2.4 eq) and KOH (85% powder, 2.4 eq). The reaction mixture was stirred at RT for 5 hr. The reaction was stopped by addition of EtOAc (25 mL). The organic phase was washed with saturated NaHCO$_3$ (3×10 mL), dried over Na$_2$SO$_4$, filtered, and evaporated to dryness. The product mixture was subjected to HPLC purification (C18-reverse phase column, solvent A: H$_2$O with 5 mM NH$_4$OAc, solvent B: CH$_3$CN/MeOH (4/1) with 5 mM NH$_4$ OAc, 58% B isocratic) to yield 20 mg of pure compound K and 10 mg of pure compound L.

Compound K: $^1$H NMR (400 MHz, CDCl$_3$) δ (ppm) 8.76 (dd, J=1.6 Hz, 4.4 Hz, 1H), 8.06 (d, J=7.2 Hz, 1H), 8.01 (d, J=9.2 Hz, 1H), 7.38 (dd, J=2.7 Hz, 9.2 Hz, 1H), 7.36 (dd, J=4.1 Hz, 8.6 Hz, 1H), 7.10 (d, J=2.8 Hz, 1H), 5.45 (br, 1H), 4.95 (br, 1H), 4.49 (d, J=7.6 Hz, 1H), 4.40 (d, J=7.6 Hz, 1H), 4.29 (m, 2H), 4.18 (dd, J=6.4 Hz, 6.4 Hz, 1H), 3.90 (dd, J=10.4 Hz, 5.1 Hz, 1H), 3.76 (d, J=11.2 Hz, 1H), 3.69 (m, 1H), 3.58 (s, 3H), 3.48 (m, 1H), 3.42 (s, 3H), 3.23 (dd, J=9.4 Hz, 9.4 Hz, 1H), 3.13 (dd, J=2.3 Hz, 9.4 Hz, 1H), 2.94 (dd, J=2.7 Hz, 7.8 Hz, 1H), 2.77 (s, 6H), 2.61 (m, 1H), 2.44 (dd, J=10.6 Hz, 16.2 Hz, 1H), 2.23 (m, 1H), 1.33 (d, J=5.9 Hz, 1H), 1.23 (d, J=6.3 Hz, 3H), 1.14 (d, J=6.6 Hz, 3H), 0.91 (d, J=6.6 Hz, 3H), 0.90 (t, J=6.3 Hz, 3H), LC-MS (m/z) calculated for C$_{58}$H$_{92}$N$_4$O$_{14}$ 1068.66. found 1069.4 (M+1).

Compound L: $^1$H NMR (400 MHz, CDCl$_3$) δ (ppm) 8.76 (dd, J=1.6 Hz, 4.4 Hz, 1H), 8.04 (d, J=7.2 Hz, 1H), 8.02 (d, J=9.2 Hz, 1H), 7.38 (dd, J=2.7 Hz, 9.2 Hz, 1H), 7.36 (dd, J=4.5 Hz, 8.0 Hz, 1H), 7.08 (d, J=2.4 Hz, 1H), 6.86 (d, J=15.6 Hz, 1H), 5.84 (d, J=15.6 Hz, 1H), 5.54 (d, J=10.4 Hz, 1H), 4.92 (dt, J=2.4 Hz, 10.0 Hz, 1H), 4.55 (d, J=7.6 Hz, 1H), 4.30 (m, 1H), 4.29 (m, 2H), 4.20 (m, 1H), 3.95 (dd, J=9.6 Hz, 4.0 Hz, 1H), 3.80 (d, J=10.0 Hz, 1H), 3.74 (dd, J=3.2 Hz, 3.2 Hz, 1H), 3.61 (s, 3H), 3.61 (m, 1H), 3.50 (m, 1H), 3.49 (s, 3H), 3.31 (m, 1H), 3.18 (dd, J=9.2 Hz, 3.2 Hz, 1H), 3.13 (d, J=9.6 Hz, 1H), 3.02 (dd, J=2.8 Hz, 8.0 Hz, 1H), 2.90 (m, 1H), 2.64 (s, 6H), 2.63 (m, 1H), 2.40 (dd, J=10.2 Hz, 16.2 Hz, 1H), 2.25 (m, 1H), 2.17 (d, J=2.4 Hz, 1H), 1.73 (s, 3H), 1.26 (d, J=6.3 Hz, 1H), 1.26 (d, J=6.3 Hz, 1H), 1.24 (d, J=6.5 Hz, 3H), 1.09 (d, J=6.8 Hz, 3H), 0.95 (d, J=6.5 Hz, 3H), 0.95 (d, J=6.5 Hz, 3H), 0.92 (t, J=7.6 Hz, 3H), 0.78 (d, J=5.9 Hz, 3H), LC-MS (m/z) calculated for C$_{58}$H$_{92}$N$_4$O$_{14}$ 1068.66. found 1069.4 (M+1).

Other compounds Ic were prepared according to the above procedure, mutatis mutandis. In some instances as noted, the E/Z oxime isomers were not separated.

Compound M. $^1$H NMR (400 MHz, CDCl$_3$) δ (ppm) 8.76 (dd, J=1.6 Hz, 4.4 Hz, 1H), 8.06 (d, J=7.2 Hz, 1H), 8.01 (d, J=9.2 Hz, 1H), 7.38 (dd, J=2.7 Hz, 9.2 Hz, 1H), 7.37 (dd, J=2.5 Hz, 6.5 Hz, 1H), 7.06 (d, J=2.5 Hz, 1H), 5.5 (br, 1H), 4.96 (br, 1H), 4.53 (d, J=7.6 Hz, 1H), 4.34 (d, J=7.8 Hz, 1H), 4.14 (m, 2H), 3.94 (br, 1H), 3.78 (d, J=10.4 Hz, 1H), 3.71 (t, J=2.74 Hz, 1H), 3.58 (m, 1H), 3.58 (s, 3H), 3.48 (m, 1H), 3.47 (s, 3H), 3.00 (dd, J=2.9 Hz, 7.8 Hz, 1H), 2.80 (m, 1H), 2.61 (s, 6H), 2.42 (dd, J=10.2 Hz, 15.6 Hz, 1H), 1.75 (s, 3H), 1.32 (d, J=6.1 Hz, 3H), 1.15 (d, J=6.8 Hz, 3H), 0.96 (d, J=6.6 Hz, 3H), 0.91 (t, J=5.7 Hz, 3H), 0.86 (d, J=6.1 Hz, 3H), LC-MS (m/z) calculated for C$_{59}$H$_{94}$N$_4$O$_{14}$ 1082.68. found 1084.0 (M+1).

Compound N $^1$H NMR (400 MHz, CDCl$_3$) δ (ppm) 8.76 (dd, J=1.6 Hz, 4.1 Hz, 1H), 8.04 (d, J=1 Hz, 8.6 Hz, 1H), 8.00 (d, J=9.2 Hz, 1H), 7.38 (dd, J=2.7 Hz, 9.4 Hz, 1H), 7.35 (dd, J=4.5 Hz, 8.6 Hz, 1H), 7.07 (d, J=2.7 Hz, 1H), 6.85 (d, J=15.6 Hz, 1H), 5.85 (d, J=15.6 Hz, 1H), 5.53 (d, J=10.4 Hz, 1H), 4.91 (dt, J=2.4 Hz, 9.8 Hz, 1H), 4.55 (d, J=7.8 Hz, 1H), 4.27 (d, J=7.2 Hz, 1H), 4.20 (m, 1H), 4.14 (m, 2H), 3.96 (dd, J=9.8 Hz, 4.1 Hz, 1H), 3.82 (d, J=9.8 Hz, 1H), 3.74 (dd, J=3.1 Hz, 3.1 Hz, 1H), 3.65 (d, J=9.8 Hz, 1H), 3.61 (s, 3H), 3.48 (s, 3H), 3.49 (m, 1H), 3.30 (m, 1H), 3.18 (dd, J=9.6 Hz, 3.1 Hz, 1H), 3.09 (dd, J=9.2 Hz, 9.2 Hz,1H), 3.02 (dd, J=2.7 Hz, 7.8 Hz, 1H), 2.91 (m, 2H), 2.56 (s, 6H), 1.74 (s, 3H), 1.08 (d, J=7.4 Hz, 3H), LC-MS (m/z) calculated for C$_{59}$H$_{94}$N$_4$O$_{14}$ 1082.68. found 1084.0 (M+1).

Compound O. The E and Z isomers were not separated. $^1$H NMR (400 MHz, CDCl$_3$) δ (ppm) 7.25 (m, 2H), 6.91 (m, 3H), 5.54 (br, 1H), 4.88 (br, 1H), 4.54 (d, J=7.4 Hz, 1H), 4.37 (m, 1H), 4.26 (m, 1H), 4.20 (m, 2H), 3.96 (br, 1H), 3.78 (br, 1H), 3.71 (dd, J=3.3 Hz, 3.3 Hz, 1H), 3.59 (s, 3H), 3.59 (m, 1H), 3.49 (m, 1H), 3.46 (s, 3H), 3.29 (m, 1H), 3.15 (br, 1H), 2.49 (s, 6H), 2.36 (dd, J=10.2 Hz, 10.2 Hz, 1H), 1.73 (s, 3H), 1.14 (d, J=6.5 Hz, 3H), 0.80 (d, J=6.1 Hz, 3H), LC-MS (m/z) calculated for C$_{54}$H$_{89}$N$_4$O$_{14}$ 1003.63. found 1005.0 (M+1).

Compound P. $^1$H NMR (400 MHz, CDCl$_3$) δ (ppm) 7.30 (m, 2H), 7.01 (dd, J=8.6 Hz, 8.6 Hz, 2H), 5.5 (br, 1H), 4.95 (br, 1H), 4.53 (d, J=7.8 Hz, 1H), 4.31 (d, J=7.2 Hz, 1H), 3.78 (d, J=10.0 Hz, 1H), 3.73 (t, J=2.9 Hz, 1H), 3.60 (s, 3H), 3.43 (s, 3H), 3.17 (dd, J=3.3 Hz, 9.4 Hz, 1H), 3.08 (dd, J=9.6 Hz, 9.6 Hz, 1H), 3.00 (dd, J=2.7 Hz, 7.6 Hz, 1H), 2.95 (m, 1H), 2.56 (s, 6H), 1.88 (m, 1H), 1.75 (s, 3H), 1.57 (m, 2H), 1.30 (d, J=6.3 Hz, 3H), 1.13 (d, J=6.9 Hz, 3H), LC-MS (m/z) calculated for C$_{53}$H$_{86}$FN$_3$O$_{13}$ 991.61. found 993.0 (M+1).

Compound Q. $^1$H NMR (400 MHz, CDCl$_3$) δ (ppm) 7.35 (d, 8.4 Hz, 1H), 7.33 (d, J=8.4 Hz, 1H), 7.05 (d, J=8.8 Hz, 1H), 7.03 (d, J=8.4 Hz, 1H), 6.88 (d, J=15.6 Hz, 1H), 5.82 (d, J=15.6 Hz, 1H), 5.58 (d, J=10.4 Hz, 1H), 4.95 (dt, J=10 Hz, 2.4 Hz, 1H), 4.55 (d, J=8 Hz, 1H), 4.33 (d, J=5.6 Hz, 1H), 3.96 (dd, J=4 Hz, 9.6 Hz, 1H), 3.84 (d, J=10 Hz, 1H), 3.75 (dd, J=2.8 Hz, 2.8 Hz, 1H), 3.69 (d, J=8 Hz, 1H), 3.63 (s, 3H), 3.48 (s, 3H), 3.49 (m, 1H), 3.32 (m, 1H), 3.18 (m, 2H), 3.03 (dd, J=7.6 Hz, 2.8 Hz, 1H), 2.91 (m, 1H), 2.73 (s, 6H), 2.43 (dd, J=16.0 Hz, 10.0 Hz, 1H), 1.75 (s, 3H), 1.60 (m, 2H), 1.52 (m, 2H), 1.28 (d, J=6.4 Hz, 3H), 1.26 (d, J=6.4 Hz, 3H), 1.07 (d, J=6.8 Hz, 3H), 0.96 (d, J=6.8 Hz, 3H), 0.93 (t, J=7.2 Hz, 3H), 0.93 (d, J=6.4 Hz, 3H), 0.85 (d, J=6.4 Hz, 3H), LC-MS (m/z) calculated for C$_{53}$H$_{86}$FN$_3$O$_{13}$ 991.61. found 993.06 (M+1).

Compound CC. $^1$H NMR (400 MHz, CDCL$_3$) δ (ppm) 8.77 (dd, J=1.57 Hz, 4.11 Hz, 1H), 8.04 (d, J=7.2 Hz, 1H), 8.02 (d, J=9.2 Hz, 1H), 7.38 (dd, J=2.7 Hz, 7.6 Hz, 1H), 7.36 (dd, J=4.3 Hz, 8.4 Hz, 1H), 7.08 (d, J=2.9 Hz, 1H), 6.86(d, J=15.6 Hz, 1H), 5.84 (d, J=15.6 Hz, 1H), 5.54 (d, J=10.2 Hz, 1H), 4.92 (m, 1H), 4.55 (d, J=7.63 Hz, 1H), 4.32 (m, 1H), 4.29 (m, 2H), 4.20 m, 2H), 3.96 (dd, J=4.3 Hz, 9.4 Hz, 1H), 3.80 (d, J=10.0 Hz, 1H), 3.74 (dd, J=3.1 Hz, 3.1 Hz, 1H), 3.62 (m, 1H), 3.61 (s, 3H), 3.52 (m, 1H), 3.49 (s, 3H), 3.31 (m, 1H), 3.18 (dd, J=3.2 Hz, 9.2 Hz, 1H), 3.13 (d, J=9.4 Hz, 1H), 3.02 (dd, J=2.5 Hz, 7.6 Hz, 1H), 2.90 (m, 2H), 2.64 (m, 1H), 2.64 (s, 6H), 2.40 (dd, J=10.6 Hz, 16.4 Hz, 1H), 2.25 (m, 2H), 2.17 (d, J=2.54 Hz, 1H), 1.95 (d, J=15.9 Hz, 1H), 1.88 (m, 1H), 1.73 (s, 3H), 1.26 (d, J=6.1 Hz, 3H), 1.24 (d, J=6.6 Hz, 3H), 1.09 (d, J=6.85 Hz, 3H), 0.95 (d, J=6.6 Hz, 3H), 0.92 (t, J=7.4 Hz, 3H), 0.78 (d, J=6.6 Hz, 3H), LC-MS (m/z) calculated for C$_{58}$H$_{92}$N$_4$O$_{14}$, 1068.66. found 1069.74 (M+1).

EXAMPLE 3

Compounds Id

Compounds Id were prepared as shown in FIG. 3. The procedures were analogous to those used for compounds Ic, except that OMT 1 was used instead of tilmicosin 6. See Debono et al., *J. Antibiot.* 42 (8), 1253-1267 (1989). The E and Z isomers were separated, except where noted otherwise.

Compound R. $^1$H NMR (400 MHz, CDCl$_3$) δ (ppm) 8.76 (d, J=2.8 Hz, 2H), 8.03 (d, J=8.0 Hz,1H), 8.00 (d, J=9.2 Hz, 1H), 7.35 (m, 2H), 7.08 (d, J=2 Hz, 1H), 6.71 (d, J=16.8 Hz, 1H), 6.61 (d, J=16.8, 1H), 5.57 (d, J=10.4 Hz, 1H), 4.77 (m, 1H), 2.79 (s, 6H), 1.78 (s, 3H), LC-MS (m/z) calculated for $C_{50}H_{78}N_4O_{10}$ 894.57. found 896.0 (M+1).

Compound S. $^1$H NMR (400 MHz, CDCl$_3$) δ (ppm) 8.77 (br, 1H), 8.01 (d, J=9.2 Hz, 1H), 8.00 (d, J=8.0 Hz, 1H), 7.37 (d, J=5.6 Hz, 1H), 7.36 (d, J=6.4 Hz, 1H), 7.05 (d, J=2.4 Hz, 1H), 6.68 (d, J=16.8 Hz, 1H), 6.07 (d, J=17.2 Hz, 1H), 5.46 (d, J=10.8 Hz, 1H), 4.82 (dd, J=11.2 Hz, 11.2 Hz, 1H), 1.22 (d, J=7.2 Hz, 3H), 1.04 (d, J=6.4 Hz, 3H), 0.97 (t, J=7.6 Hz, 3H), 0.94 (d, 6.4 Hz, 3H), 0.73 (d, J=6.4 Hz, 3H), LC-MS (m/z) calculated for $C_{50}H_{78}N_4O_{10}$ 894.57. found 896.0 (M+1).

Compound T. $^1$H NMR (400 MHz, CDCl$_3$) δ (ppm) 8.73 (d, J=4.4 Hz, 2H), 8.01 (d, J=8.0 Hz,1H), 7.97 (d, J=9.6 Hz, 1H), 7.34 (m, 2H), 7.03 (d, J=2.8 Hz, 1H), 5.45 (d, J=10.4 Hz, 1H), 2.59 (s, 6H), 1.74, LC-MS (m/z) calculated for $C_{51}H_{80}N_4O_{10}$ 908.59. found 910.0 (M+1).

Compound U. $^1$H NMR (400 MHz, CDCl$_3$) δ (ppm) 8.76 (d, J=2.8 Hz, 1H), 8.03 (d, J=7.2 Hz, 1H), 8.00 (d, J=9.6 Hz, 1H), 7.35 (m, J=5.6 Hz, 2H), 7.05 (d, J=2.8 Hz, 1H), 6.64 (d, J=16.8 Hz, 1H), 6.06 (d, J=17.2 Hz, 1H), 5.44 (d, J=10.0 Hz, 1H), 4.80 (m, 1H), 2.62 (s, 6H), 1.79 (s, 3H), LC-MS (m/z) calculated for $C_{51}H_{80}N_4O_{10}$ 908.59. found 910.0 (M+1).

Compound V. The E and Z isomers were not separated. $^1$H NMR (400 MHz, CDCl$_3$) δ (ppm), 7.28 (m, 2H), 6.93 (m, 3H), 6.85 (d, J=15.6 Hz, 1H), 5.91 (d, J=15.6 Hz, 1H), 2.52 (s, 6H), 1.78 (s, 3H), 1.16 (d, J=6.8 Hz, 3H), 1.07 (d, J=6.8 Hz, 3H), 0.81 (d, J=6.4 Hz, 3H), LC-MS (m/z) calculated for $C_{46}H_{75}N_3O_{10}$ 829.55. found 831.0 (M+1).

Compound W. The E and Z isomers were not separated. $^1$H NMR (400 MHz, CDCl$_3$) δ (ppm), 7.27 (m, 2H), 7.00 (m, 3H), 2.50 (s, 6H), 1.77 (s, 3H), 1.12 (d, J=6.4 Hz, 3H), 0.95 (d, J=6.8 Hz, 3H), LC-MS (m/z) calculated for $C_{45}H_{72}FN_3O_9$ 817.55. found 819.0 (M+1).

Compound X. The E and Z isomers were not separated. $^{13}$C NMR (100 MHz, CDCl$_3$) δ (ppm), 177.02, 167.38, 150.86, 136.99, 129.25, 120.63, 116.66, 73.26, 72.41, 72.07, 58.15, 49.77, 49.39, 46.78, 44.90, 41.83, 41.64, 40.36, 39.39, 28.67, 22.68, 19.04, 18.14, 12.73, 9.71, LC-MS (m/z) calculated for $C_{50}H_{81}N_5O_{10}$ 911.60. found 913.0 (M+1).

EXAMPLE 4

Compounds Ie

Compounds Ie were prepared according to FIG. 4, with the following procedure for converting compound A to compounds Y and Z being representative.

Step 1: Phosphate ester 10. Compound A (218 mg, 0.26 mmol, 1 eq) was flushed under N$_2$ for 30 min. Freshly distilled THF (0.5 mL) was added followed by 1,8-diazabicyclo[5.4.0]undec-7-ene ("DBU," 38.7 µL, 1 eq), and diphenylphosphorylazide (61.5 µL, 1.1 eq). The reaction mixture was stirred at RT for 2 hr. TLC (10% MeOH in CH$_2$Cl$_2$) indicated the starting material was consumed and a new upper spot appeared. Solvent was removed under vacuum. Separation of the product using silica gel column on ISCO (1% Et$_3$N in CH$_2$Cl$_2$ to 1% Et$_3$N to 1% MeOH in CH$_2$Cl$_2$) to yield 173 mg of phosphate ester 10.

Step 2: 23-Azido Compound 11. Phosphate ester 10 (173 mg, 1 eq) was dissolved in DMF (3.2 mL). NaN$_3$ (314 mg, 30 eq) was added. The reaction mixture was heated to 50° C. The reaction progress was monitored by HPLC (C-18 reverse phase column, 4.6×150 mm, mobile phase: isocratic 60% B, solvent B: CH$_3$CN/MeOH (4/1) with 5 mM NH$_4$OAc; solvent A: H$_2$O with 5 mM NH$_4$OAc). HPLC indicated the reaction was 50% complete after stirring at 50° C. for 3.5 hours. NaI (23.8 mg) was added and the reaction mixture was stirred at 50° C. for another 2.5 hr. HPLC indicated the reaction was still not complete. NaN$_3$ (208 mg) was added and the reaction was stirred at 65° C. overnight until HPLC shown that little starting material remained. EtOAc (100 mL) was added and the organic layer was washed with saturated NaHCO$_3$ (3×30 mL), dried over Na$_2$SO$_4$, filtered, and evaporated to dryness. 23-Azido compound 11 (119 mg) was obtained after purification on ISCO using a 10 g silica gel column (1% Et$_3$N in CH$_2$Cl$_2$ to 1% Et$_3$N to 1% MeOH in CH$_2$Cl$_2$).

Step 3: Amine 12. To a solution of 23-azido compound 11 (50 mg, 1 eq) in THF (5 mL) and H$_2$O (0.25 mL) was added Me$_3$P (225 µL, 1M in THF). The reaction mixture was stirred at RT for 1.5 hr until HPLC (C-18 reverse phase column, 4.6×150 mm, mobile phase: isocratic 60% B, solvent B: CH$_3$CN/MeOH (4/1) with 5 mM NH$_4$OAc; solvent A: H$_2$O with 5 mM NH$_4$OAc) indicated the starting material was completely converted. The solvent was removed to yield amine 12, which was used for next step without purification.

Step 4: Dimethyl amine 13. Amine 12 was dissolved in MeOH (3 mL). H$_2$CO (182 µL, 20 eq), HOAc (24.6 µL, 8 eq), and NaCNBH$_3$ (14.5 mg, 4 eq) were added. The reaction mixture was stirred at RT for 1 hr. The volatiles were removed under vacuum. The products were purified directly on a reverse phase HPLC semi-prep column (C-18 reverse phase, 9.6×250 mm, the mobile phase B: CH$_3$CN/MeOH (4/1) with 5 mM NH$_4$OAc; phase A: H$_2$O with 5 mM NH$_4$OAc, isocratic 45% B, diode array detector 190-400 nm) to yield 15.6 mg of dimethylamine 13 (E oxime) and 12.3 mg of dimethylamine 13 (Z oxime).

Step 5a: Compound Y. Dimethylamine 13 E oxime (15.6 mg) was dissolved in acetone (2 mL). CSA(16 mg) was added. The reaction was stirred at RT overnight. The solvent was removed and the product was purified by silica gel column on ISCO (1% Et$_3$N in CH$_2$Cl$_2$ to 1% Et$_3$N to 2% MeOH in CH$_2$Cl$_2$) to yield 11 mg compound Y. The final compound was characterized by NMR ($^1$H, $^{13}$C, COSY, HSQC, HMBC) and LC/MS. $^1$H NMR (400 MHz, CDCl$_3$), δ (ppm) 9.64 (s, 1H), 8.73 (d, J=2.8 Hz, 1H), 8.10 (d, J=8.4 Hz, 1H), 7.98 (d, J=9.2 Hz, 1H), 7.38 (dd, J=2.4 Hz, 9.2 Hz, 1H), 7.33 (dd, J=4.0 Hz, 8.0 Hz, 1H), 7.10 (d, J=2.4 Hz, 1H), 6.90 (d, J=15.6 Hz, 1H), 5.79 (d, J=15.6 Hz, 1H), 5.33 (d, J=10.0 Hz, 1H), 4.66 (dd, 1H), 4.25 (m, 4H), 4.12 (m, 2H), 3.92 (d, J=10.8 Hz, 1H), 3.74 (d, J=10.0 Hz, 1H), 3.53 (m, 1H), 3.47 (m, 1H), 3.02 (dd, J=9.2 Hz, 9.2 Hz, 1H), 2.90 (dd, J=10.8 Hz, 18.0 Hz, 1H), 2.76 (m, 1H), 2.49 (s, 6H), 2.35 (m, 2H), 2.18 (m, 1H), 2.19 (d, 1H), 1.82 (m, 1H), 1.75 (s, 3H), 1.58 (m, 1H), 1.39 (m, 1H), 1.17 (d, J=6.0 Hz, 3H), 1.08 (d, J=6.8 Hz, 3H), 1.00 (d, J=6.4 Hz, 3H), 0.92 (t, J=7.2, 3H), $^{13}$C NMR (100 MHz, CDCl$_3$), δ (ppm), 203.6, 174.3, 159.8, 157.0, 147.7, 144.2, 138.4, 138.1, 135.0, 134.5, 130.6, 129.4, 122.6, 121.2, 116.3, 105.8, 103.7, 80.4, 77.9, 73.2, 71.0, 70.7, 70.2, 70.0, 64.9, 61.2, 45.7, 43.7, 43.0, 41.7, 39.1, 31.9, 29.6, 29.0, 27.2, 25.7, 18.7, 17.9, 12.6, 9.8, 9.1, LC-MS (m/z) calculated for $C_{45}H_{68}N_4O_{10}$ 824.49. found 825.5 (M+1).

Step 5b: Compound Z. Dimethylamine 13 Z oxime (12.3 mg) was dissolved in acetone (2 mL). CSA(13 mg) was added. The reaction was stirred at RT for 36 hr. Solvent was removed and the product was purified by silica gel column on ISCO (1% $Et_3N$ in methylene chloride to 1% $Et_3N$ to 2% MeOH in $CH_2Cl_2$) to obtain 8 mg compound Z. $^1$H NMR (400 MHz, $CDCl_3$), δ (ppm), 9.72 (s, 1H), 8.74 (d, J=3.6 Hz, 1H), 8.14 (d, J=7.6 Hz, 1H), 7.98 (d, J=9.2 Hz, 1H), 7.40 (dd, J=2.0 Hz, 9.2 Hz, 1H), 7.33 (dd, J=4.0 Hz, 8.0 Hz, 1H), 7.18 (s, 1H), 5.13 (d, J=9.2 Hz, 1H), 4.49 (br, 1H), 4.29 (m, 4H), 4.18 (m, 2H), 3.87 (d, J=10.4 Hz, 1H), 3.79 (m, 1H), 3.53 (m, 1H), 3.47 (m, 1H), 3.05 (dd, J=9.2 Hz, 9.2 Hz, 1H), 2.51 (s, 6H), 1.73 (s, 3H), 1.15 (d, J=6.0 Hz, 3H), LC-MS (m/z) calculated for $C_{45}H_{68}N_4O_{10}$ 824.49. found 825.5 (M+1).

EXAMPLE 5

Compounds If

Compounds If were made using the procedure of Example 1, except that the starting material was desmycosin 5 instead of OMT 1.

Compound AA. $^1$H NMR (400 MHz, $CDCl_3$) δ (ppm) 9.64 (s, 1H), 8.74 (d, J=3.6 Hz, 1H), 8.08 (d, J=8.0 Hz, 1H), 7.99 (d, J=9.2 Hz, 1H), 7.37 (dd, J=2.4 Hz, 8.8 Hz, 1H), 7.33 (dd, J=4.0 Hz, 8.0 Hz, 1H), 7.1 (d, J=2.8 Hz, 1H), 6.89 (d, J=15.6 Hz, 1H), 5.83 (d, J=16 Hz, 1H), 5.55 (d, J=10.4 Hz, 1H), 4.94 (ddd, 1H), 4.54 (d, J=8 Hz, 1H), 4.27 (m, 3H), 4.23 (d, J=7.43 Hz, 1H), 4.15 (m, 3H), 3.92 (m, 2H), 3.74 (m, 2H), 3.61 (s, 3H), 3.49 (s, 3H), 2.50 (s, 6H), 1.73 (s, 3H), 1.26 (d, 3H), 1.18 (d, J=6.65 Hz, 3H), 1.09 (d, J=6.46 Hz, 3H), 0.99 (d, J=6.46 Hz, 3H), 0.93 (t, J=7.24 Hz, 3H), LC-MS (m/z) calculated for $C_{51}H_{77}N_3O_{15}$ 971.54. found 972.79 (M+1).

Compound BB. $^1$H NMR (400 MHz, $CDCl_3$) δ (ppm) 9.73 (s, 1H), 8.76 (d, J=2.8 Hz, 1H), 8.10 (d, J=8.4 Hz, 1H), 8.0 (d, J=9.2 Hz, 1H), 7.41 (dd, J=2.4 Hz, 9.2 Hz, 1H), 7.34 (dd, J=4.4 Hz, 8.4 Hz, 1H), 7.15 (d, J=2.4 Hz, 1H), 5.41 (d, J=10.0 Hz, 1H), 4.84 (m, 1H), 4.49 (d, J=7.6 Hz, 1H), 3.61 (s, 3H), 3.42 (s, 3H), 2.51 (s, 6H), 1.75 (s, 3H), 1.18 (d, J=6.85 Hz, 3H), LC-MS (m/z) calculated for $C_{51}H_{77}N_3O_{15}$ 971.54. found 973.2 (M+1).

EXAMPLE 6

Compounds Ig

Compound HH, representative of compounds Ig, was made from compound 14 (desmycarosyl niddamycin). Compound 14 can be made by the acid treatment of niddamycin (Ma et al., US 2004/0014687 (2004), incorporated herein by reference). The sequence of reactions was analogous to that in FIG. 1 (protection of C-19 aldehyde, oximation of C-9 ketone, O-alkylation of C-9 oxime, and deprotection of C-19 aldehyde).

EXAMPLE 7

Compounds Ih

Figure 5:
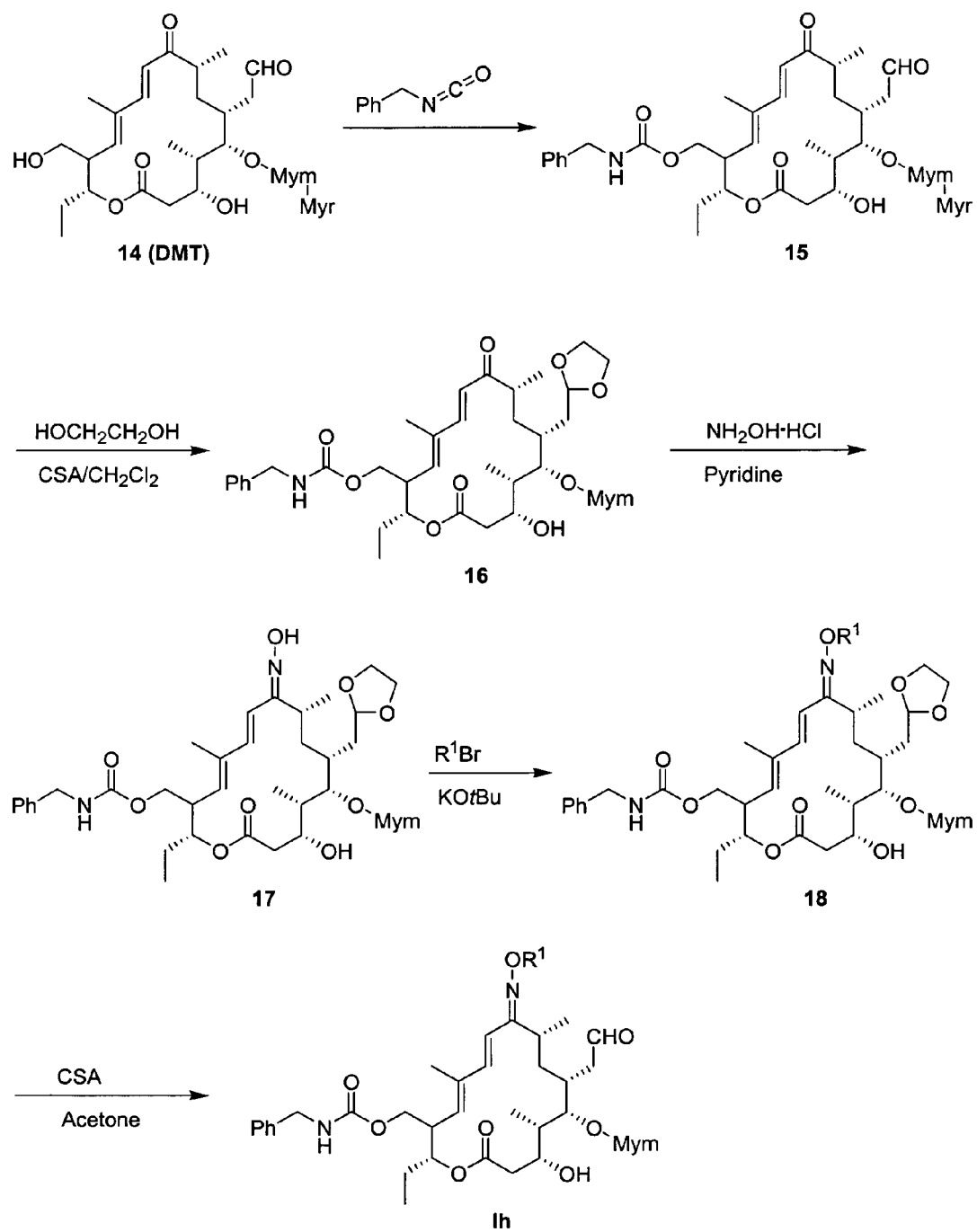

FIG. 5 shows the scheme for the preparation of compounds Ih, using the instance in which $Ar^1$ is phenyl as the archetype.

Step 1: Keto carbamate 15. To demycinosyltylosin 14 ("DMT", 2 g) in 17 mL of dichloromethane at room temperature, was added benzylisocyanate (0.83 mL). The reaction was stirred at room temperature for 7 hours. DMT can be made, for example, as described in Baltz et al., U.S. Pat. No. 4,321,361 (1982), the disclosure of which is incorporated herein by reference. TLC indicated the starting material was still present. Therefore, the reaction was stirred over night at room temperature. The solvent was removed under reduced pressure. The product was purified by silica gel column (5% acetone in hexane to 50% acetone in hexane with 1% triethylamine), yielding keto carbamate 15 (1.84 g).

Step 2: Acetal carbamate 16. The reaction mixture of 2.05 g of keto carbamate 15, 2.9 g ethylene glycol, 0.814 g CSA in methylene chloride (20 mL), was stirred at room temperature overnight. Ethyl acetate (300 mL) was added. The organic layer was washed with saturated $NaHCO_3$ (2×180 mL), dried over sodium sulfate, filtered and evaporated to dryness, yielding acetal carbamate 16 (1.95 g).

Step 3: Oxime carbamate 17. To acetal carbamate 16 (1 g) in methanol, was added pyridine (1.07 mL) and hydroxylamine hydrochloride (0.92 g). The reaction mixture was stirred at room temperature for 8 hours. Ethyl acetate (300 mL) was added. The organic phase was washed with saturated $NaHCO_3$ (2×150 mL) and then brine (150 mL), dried over sodium sulfate, filtered and evaporated to dryness. The product was purified by silica gel column (5% acetone in hexane to 50% acetone in hexane with 1% triethylamine), yielding oxime carbamate 17 (1 g).

Step 4: Alkylated oxime carbamate 18. To oxime carbarnate 17 (150 mg, 0.195 mmol)and an alkyl bromide (0.411 mmol) in THF(3 mL)/DMF(1 mL) was added potassium t-butoxide (253 µL, 1M in THF) at room temperature. The reaction mixture was stirred at room temperature for 2 hours. Chloroform (120 mL) was added and the organic phase was washed with saturated $NaHCO_3$ (2×150 mL) and then brine (150 mL), dried over sodium sulfate, filtered and evaporated to dryness. Silica gel column purification (20% acetone in hexane to 80% acetone in hexane with 1% triethylamine) yielded alkylated oxime carbamate 18 (110 mg).

Step 5: Compounds Ih. Alkylated oxime carbamate 18 (20 mg), CSA (10 mg), and acetone (1 mL) were stirred together at room temperature for 2 days. The acetone was then removed. The product was purified by silica gel column (DCM w/1% TEA to 1-3% methanol in dichloromethane w/1% TEA) to yield compound Ih (15 mg).

Compounds DD, EE, and FF were prepared according to the above procedure. Compound GG was also so prepared, except that the acetal group of oxime carbamate was directly hydrolyzed, by-passing the alkylation step.

Compound DD. LC-MS (m/z) calculated for $C_{51}H_{70}N_4O_{12}$ 930.50. found 931.4 (M+1).

Compound EE. LC-MS (m/z) calculated for $C_{52}H_{72}N_4O_{12}$ 944.5 1. found 945.5 (M+1).

Compound FF. LC-MS (m/z) calculated for $C_{51}H_{68}N_4O_{11}$ 912.49. found 913.4 (M+1).

Compound GG. LC-MS (m/z) calculated for $C_{39}H_{59}N_3O_{11}$ 745.42. found 746.4 (M+1). (Compound not pure.)

EXAMPLE 8

Biological Activity

Compounds of this invention were tested for biological activity against a series of bacterial strains, using erythromycin A, tylosin, OMT, tilmicosin (compound 6, FIG. 2)), compound 8 (FIG. 3) and/or telithromycin (Ketek™) as comparison compounds. Results for *S. pneumoniae, S. aureus, S. epidermidis*, and *E. faecalis* are provided in Table B. Data on activity against *H. influenzae* for selected compounds are presented in Table C.

TABLE B

Biological Activity

| Bacteria & strain | Compound |  |  |  |  |  |  |
|---|---|---|---|---|---|---|---|
|  | Ery A | Tyl | OMT | A | B | IIa | IIb |
| *S. pneumoniae* |  |  |  |  |  |  |  |
| ATCC6301 | 0.025 | 0.098 | 0.025 | 0.025 | 0.025 | 0.20 | 0.025 |
| ATCC700671 | 0.049 | 0.20 | 0.049 | 0.025 | 0.025 | 0.39 | 0.20 |
| ATCC700676* | 6.25 | 0.20 | 0.78 | 0.025 | 0.025 | 0.20 | 0.025 |
| ATCC700677* | 6.25 | >12.5 | 6.25 | 0.20 | 0.39 | 3.12 | 1.56 |
| ATCC700905* | 3.12 | 0.20 | 0.78 | 0.025 | 0.025 | 0.39 | 0.20 |
| ATCC700906* | >12.5 | >12.5 | >12.5 | >12.5 | >12.5 | >12.5 | >12.5 |
| ATCC49619 | 0.049 | 0.098 | 0.098 | 0.01 | 0.01 | 0.20 | 0.20 |
| *S. aureus* |  |  |  |  |  |  |  |
| ATCC6538p | 0.098 | 0.20 | 0.39 | 0.025 | 0.20 | 0.78 | 0.39 |
| ATCC33591* | >12.5 | >12.5 | >12.5 | >12.5 | >12.5 | >12.5 | >12.5 |
| ATCC14154* | >12.5 | 1.56 | 1.56 | 0.20 | 0.78 | 1.56 | 1.56 |
| ATCCBAA-39* | >12.5 | >12.5 | >12.5 | >12.5 | >12.5 | >12.5 | >12.5 |
| ATCCBAA-44* | >12.5 | >12.5 | >12.5 | >12.5 | >12.5 | >12.5 | >12.5 |
| ATCC29213 | 0.20 | 1.56 | 0.78 | 0.098 | 0.78 | 1.56 | 1.56 |
| *S. epidermidis* |  |  |  |  |  |  |  |
| ATCC12228 | 0.20 | 0.39 | 0.39 | 0.098 | 0.20 | 1.56 | 0.78 |
| *E. faecalis* |  |  |  |  |  |  |  |
| ATCC51575 | >12.5 | >12.5 | >12.5 | >12.5 | >12.5 | >12.5 | >12.5 |

*macrolide resistant strain
Ery A = erythromycin A  Tyl = tylosin

| Bacteria & strain | Compound |  |  |  |  |  |  |
|---|---|---|---|---|---|---|---|
|  | C | D | E | F | G | H | J |
| *S. pneumoniae* |  |  |  |  |  |  |  |
| ATCC6301 | 0.025 | 0.025 | 0.025 | 0.025 | 0.025 | 0.025 | 0.025 |
| ATCC700671 | 0.025 | 0.049 | 0.025 | 0.049 | 0.025 | 0.049 | 0.025 |
| ATCC700676* | 0.39 | 0.049 | 0.025 | 0.049 | 0.049 | 0.049 | 0.025 |
| ATCC700677* | 6.25 | >12.5 | >12.5 | >12.5 | >12.5 | >12.5 | 0.025 |
| ATCC700905* | 0.20 | 0.049 | 0.049 | 0.049 | 0.049 | 0.049 | 0.025 |
| ATCC700906* | >12.5 | >12.5 | >12.5 | >12.5 | >12.5 | >12.5 | >12.5 |
| ATCC49619 | 0.01 | 0.049 | 0.025 | 0.025 | 0.025 | 0.025 | 0.049 |
| *S. aureus* |  |  |  |  |  |  |  |
| ATCC6538p | 0.78 | 0.098 | 0.098 | 0.098 | 0.20 | 0.20 | 0.025 |
| ATCC33591* | >12.5 | >12.5 | >12.5 | >12.5 | >12.5 | >12.5 | >12.5 |
| ATCC14154* | 1.56 | 0.78 | 0.39 | 0.39 | 0.78 | 0.39 | 0.20 |
| ATCCBAA-39* | >12.5 | >12.5 | >12.5 | >12.5 | >12.5 | >12.5 | >12.5 |
| ATCCBAA-44* | >12.5 | >12.5 | >12.5 | >12.5 | >12.5 | >12.5 | >12.5 |
| ATCC29213 | 1.56 | 0.39 | 0.39 | 0.39 | 0.78 | 0.39 | 0.20 |
| *S. epidermidis* |  |  |  |  |  |  |  |
| ATCC12228 | 0.20 | 0.20 | 0.098 | 0.049 | 0.39 | 0.20 | 0.20 |
| *E. faecalis* |  |  |  |  |  |  |  |
| ATCC51575 | >12.5 | >12.5 | >12.5 | >12.5 | >12.5 | >12.5 | >12.5 |

TABLE B-continued

Biological Activity

*Macrolide resistant strain

| Bacteria & strain | Compound |  |  |  |  |  |  |
|---|---|---|---|---|---|---|---|
|  | Tilm | K | L | M | N | O | P |
| *S. pneumoniae* |  |  |  |  |  |  |  |
| ATCC6301 | 0.39 | 0.01 | 0.01 | 0.01 | 0.025 | 0.39 | 0.39 |
| ATCC700671 | 0.78 | 0.025 | 0.01 | 0.01 | 0.049 | 0.39 | 0.78 |
| ATCC700676* | 0.78 | 0.049 | 0.049 | 1.56 | 1.56 | 1.56 | 3.12 |
| ATCC700677* | 6.25 | 0.049 | 0.025 | 6.25 | 6.25 | 6.25 | 6.25 |
| ATCC700905* | 1.56 | 0.20 | 0.098 | 1.56 | 0.78 | 0.78 | 3.12 |
| ATCC700906* | >12.5 | >12.5 | >12.5 | >12.5 | >12.5 | 12.5 | 12.5 |
| ATCC49619 | 1.56 | 0.098 | 0.025 | 0.01 | 0.098 | 0.78 | 0.78 |
| *S. aureus* |  |  |  |  |  |  |  |
| ATCC6538p | 0.098 | 0.20 | 0.20 | 0.78 | 0.78 | 0.20 | 0.39 |
| ATCC33591* | >12.5 | >12.5 | >12.5 | >12.5 | >12.5 | >12.5 | >12.5 |
| ATCC14154* | 0.39 | 0.39 | 0.20 | 1.56 | 1.56 | 0.78 | 6.25 |
| ATCCBAA-39* | >12.5 | >12.5 | >12.5 | >12.5 | >12.5 | >12.5 | >12.5 |
| ATCCBAA-44* | >12.5 | >12.5 | >12.5 | >12.5 | >12.5 | >12.5 | >12.5 |
| ATCC29213 | 0.20 | 0.39 | 0.20 | 1.56 | 3.12 | 0.39 | 0.78 |
| *S. epidermidis* |  |  |  |  |  |  |  |
| ATCC12228 | 0.098 | 0.39 | 0.20 | 1.56 | 3.12 | 0.39 | 0.78 |
| *E. faecalis* |  |  |  |  |  |  |  |
| ATCC51575 | >12.5 | >12.5 | >12.5 | >12.5 | >12.5 | >12.5 | >12.5 |

*Macrolide resistant strain
Tilm = tilmicosin (Compound 6, FIG. 2)

| Bacteria & strain | Compound |  |  |  |  |  |  |
|---|---|---|---|---|---|---|---|
|  | 8 | Q | R | S | T | U | V |
| *S. pneumoniae* |  |  |  |  |  |  |  |
| ATCC6301 | 0.39 | 0.20 | 6.25 | 6.25 | 1.56 | 6.25 | 0.20 |
| ATCC700671 | 0.78 | 0.39 | 6.25 | 6.25 | 3.12 | 12.5 | 0.39 |
| ATCC700676* | 1.56 | 0.78 | >12.5 | 12.5 | 6.25 | >12.5 | 0.78 |
| ATCC700677* | >12.5 | 6.25 | >12.5 | >12.5 | >12.5 | >12.5 | >12.5 |
| ATCC700905* | 1.56 | 0.78 | >12.5 | 12.5 | 6.25 | 12.5 | 0.39 |
| ATCC700906* | >12.5 | 12.5 | >12.5 | >12.5 | >12.5 | >12.5 | >12.5 |
| ATCC49619 | 0.78 | 0.39 | 6.25 | 6.25 | 6.25 | 12.5 | 0.39 |
| *S. aureus* |  |  |  |  |  |  |  |
| ATCC6538p | 0.39 | 0.20 | 12.5 | >12.5 | 6.25 | >12.5 | 0.78 |
| ATCC33591* | >12.5 | 12.5 | >12.5 | >12.5 | >12.5 | >12.5 | >12.5 |
| ATCC14154* | 1.56 | 0.78 | >12.5 | >12.5 | >12.5 | >12.5 | 6.25 |
| ATCCBAA-39* | >12.5 | >12.5 | >12.5 | >12.5 | >12.5 | >12.5 | >12.5 |
| ATCCBAA-44* | >12.5 | >12.5 | >12.5 | >12.5 | >12.5 | >12.5 | >12.5 |
| ATCC29213 | 1.56 | 0.78 | >12.5 | >12.5 | 12.5 | >12.5 | 6.25 |
| *S. epidermidis* |  |  |  |  |  |  |  |
| ATCC12228 | 0.78 | 0.78 | >12.5 | >12.5 | >12.5 | >12.5 | 6.25 |
| *E. faecalis* |  |  |  |  |  |  |  |
| ATCC51575 | >12.5 | >12.5 | >12.5 | >12.5 | >12.5 | >12.5 | >12.5 |

*Macrolide resistant strain

| Bacteria & strain | Compound |  |  |  |  |  |  |
|---|---|---|---|---|---|---|---|
|  | W | X | Y | Z | AA | BB | HH |
| *S. pneumoniae* |  |  |  |  |  |  |  |
| ATCC6301 | 0.39 | 0.049 | 0.025 | 0.025 | 0.025 | 0.025 | 0.025 |
| ATCC700671 | 0.39 | 0.098 | 0.098 | 0.049 | >12.5 | 0.049 | 0.025 |
| ATCC700676* | 0.39 | 1.56 | 0.025 | 0.025 | 0.049 | 0.049 | 0.025 |
| ATCC700677* | >12.5 | >12.5 | >12.5 | >12.5 | 6.25 | 0.025 | 3.12 |
| ATCC700905* | 0.39 | 0.78 | 0.025 | 0.025 | 6.25 | 0.025 | 0.025 |
| ATCC700906* | >12.5 | >12.5 | >12.5 | >12.5 | >12.5 | >12.5 | >12.5 |
| ATCC49619 | 0.39 | 0.049 | 0.025 | 0.049 | 6.25 | 0.049 | 0.025 |
| *S. aureus* |  |  |  |  |  |  |  |
| ATCC6538p | 0.78 | 0.39 | — | — | 0.39 | 0.2 | 0.2 |
| ATCC33591* | >12.5 | >12.5 | — | — | >12.5 | >12.5 | >12.5 |

TABLE B-continued

Biological Activity

| | | | | | | | |
|---|---|---|---|---|---|---|---|
| ATCC14154* | 3.12 | 3.12 | — | — | 0.78 | 0.78 | 0.78 |
| ATCCBAA-39* | >12.5 | >12.5 | — | — | >12.5 | >12.5 | >12.5 |
| ATCCBAA-44* | >12.5 | >12.5 | — | — | >12.5 | >12.5 | >12.5 |
| ATCC29213 | 3.12 | 1.56 | — | — | 0.78 | 0.39 | 3.12 |
| S. epidermidis | | | | | | | |
| ATCC12228 | 3.12 | 0.78 | — | — | 0.78 | 0.39 | 0.78 |
| E. faecalis | | | | | | | |
| ATCC51575 | >12.5 | >12.5 | — | — | >12.5 | >12.5 | >12.5 |

*Macrolide resistant strain

| Bacteria & strain | Compound | | | | | |
|---|---|---|---|---|---|---|
| | DD | EE | FF | GG | IIc | IId |
| S. pneumoniae | | | | | | |
| ATCC6301 | 0.049 | 0.049 | 0.2 | 0.049 | 0.2 | 0.025 |
| ATCC700671 | 0.049 | 0.2 | 0.2 | 0.098 | 0.39 | 0.2 |
| ATCC700676* | 0.049 | 0.049 | 0.049 | 0.098 | 0.2 | 0.025 |
| ATCC700677* | 0.2 | 0.39 | 0.2 | 0.39 | 3.12 | 1.56 |
| ATCC700905* | >12.5 | 0.049 | 0.098 | 0.098 | 0.39 | 0.2 |
| ATCC700906* | 0.049 | >12.5 | >12.5 | >12.5 | >12.5 | >12.5 |
| ATCC49619 | 0.049 | 0.098 | 0.2 | 0.049 | 0.2 | 0.2 |
| S. aureus | | | | | | |
| ATCC6538p | 0.78 | 3.12 | 1.56 | 3.12 | 0.78 | 0.39 |
| ATCC33591* | 12.5 | >12.5 | 12.5 | >12.5 | >12.5 | >12.5 |
| ATCC14154* | 1.56 | 6.25 | 6.25 | 6.25 | 1.56 | 1.56 |
| ATCCBAA-39* | >12.5 | >12.5 | >12.5 | >12.5 | >12.5 | >12.5 |
| ATCCBAA-44* | >12.5 | >12.5 | >12.5 | >12.5 | >12.5 | >12.5 |
| ATCC29213 | 0.78 | 6.25 | 3.12 | 0.78 | 1.56 | 1.56 |
| S. epidermidis | | | | | | |
| ATCC12228 | 0.78 | 6.25 | 3.12 | 0.39 | 1.56 | 0.78 |
| E. faecalis | | | | | | |
| ATCC51575 | >12.5 | >12.5 | >12.5 | >12.5 | >12.5 | >12.5 |

*Macrolide resistant strain

TABLE C

H. influenzae Activity

| Compound | Haemophilus Influenzae strain | | | | |
|---|---|---|---|---|---|
| | ATCC9006 | ATCC49766 | EH001 | EH002 | EH003 |
| EryA | 1.56 | 6.25 | 3.12 | 6.25 | 3.12 |
| Ketek | 1.56 | 3.12 | 1.56 | 6.25 | 1.56 |
| OMT | 1.56 | 1.56 | 3.12 | 6.25 | 1.56 |
| A | 6.25 | 6.25 | — | — | — |
| J | 6.25 | 6.25 | — | — | — |
| Y | 1.56 | 3.12 | 3.12 | 6.25 | 3.12 |
| Z | 1.56 | 3.12 | 3.12 | 3.12 | 1.56 |
| DD | 12.5 | 12.5 | — | — | — |
| EE | 12.5 | >12.5 | — | — | — |
| FF | 12.5 | 12.5 | — | — | — |
| GG | 12.5 | 12.5 | — | — | — |

The above results demonstrate that compounds of this invention are active against a variety of bacteria, such as *S. pneumoniae, S. aureus, H. influenzae, S. epidermidis*, and *E. faecalis*.

Over all, the compounds according to formula Ib have comparable or better activity than erythromycin A or OMT against macrolide-susuceptible strains, and they show substantially improved activity against a number of macrolide-resistant strains of *S. pneumoniae* (ATCC700676, ATCC700677, ATCC700905, and ATCC14154). In addition, some are also more potent than OMT against the inducibly resistant *Staphylococcus aureus* host ATCC14154. It is worth noting that the optimal atom length between the group Ar and the oxime oxygen is four, with compounds A and J (4 atom linker) showing properties superior to compound B (5 atom linker) and compounds F and G (3 atom linker). The Z-configuration oximes consistently show better activities than their E counterparts (i.e., compound IIb is more active than compound Ia and compound E is more active than compound D).

In general, compounds according to formula Ic show significantly increased antibacterial activities over the parent compound tilmicosin (compound 6, FIG. 2) against both macrolide-susceptible and macrolide-resistant *S. pneumoniae* strains.

20-Deoxy(3,5-dimethyl-1-piperidine)OMT (compound 8, FIG. 3) and 20-deoxy(3,5-dimethyl-1-piperidine)OMT 9-oxime (compound 9, FIG. 3) exhibited no antibiotic activity and addition of aromatic side chains (compounds R through X) restored antibacterial activity only slightly. Hansen et. al., *Molecular Cell* 10, 117 (2002), have suggested that the C-6 ethylaldehyde of 16-membered macrolides forms a covalent bond with the N6 atom of the A2103 residue (corresponding to A2062 in *E. coli*) in the 23S RNA component of the ribosome of *Haloarcula marismortui*. They also suggested that the mycinosyl moiety of tylosin interacts with A841 (A748 in *E. coli* numbering) in domain II of the 50S ribosome. It is possible that the binding of 16-membered macrolides to ribosomes requires the mycinose residue if the 19-aldehyde is missing (hence the failure of compound 25 to bind) and the addition of extensions at C-9 do not restore binding substantially. On the other hand, where the scaffold contains either the C-19 aldehyde (OMT) or the mycinose residue (tilmicosin), addition of arylalkyl side chains at C-9 appears to enhance binding to ribosomes.

Regarding the *H. influenzae* in Table C, compounds A and J showed approximately a 4-fold decrease in activity compared to OMT against strains ATCC9006 and ATCC49766 (Table C). It has been reported that replacement of the 23-OH of OMT by a basic group such as dialkylamine enhances its potency against gram-negative bacteria. (See Sakamoto et al., *J. Antibiotics* 37 (12), 1628 (1984) and Tanaka et al., *J. Antibiotics* 35 (1), 113 (1984).) Compounds Y and Z, which may be viewed as 23-deoxy-23-dimethylamino counterparts of compound A, were found to have improved potency against *H. influenzae*, to a level similar to OMT and Ketek™, while their potency against *S. pneumoniae* essentially remained unchanged, compared to compound A (except against ATCC700677).

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

The invention claimed is:

1. A compound having a structure according to formula I

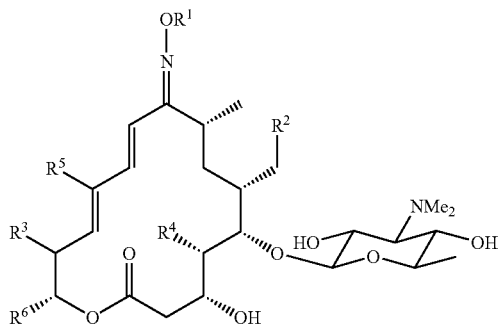

and the pharmaceutically acceptable salts thereof, wherein $R^1$ is H,

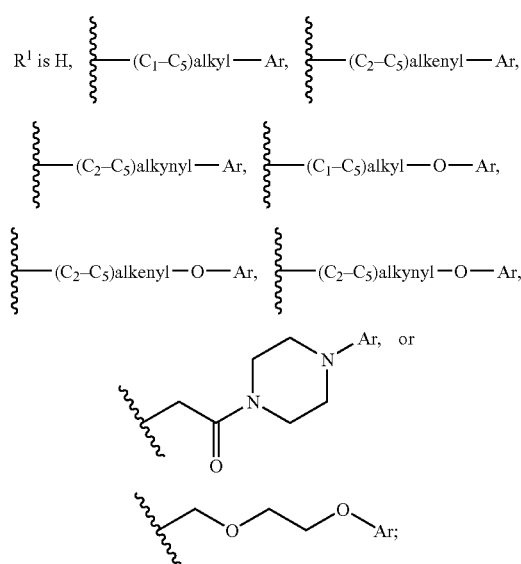

$R^2$ is CHO or

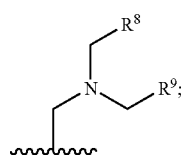

$R^3$ is H, $CH_2OH$,

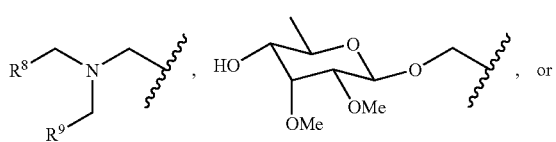

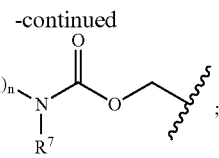

$R^4$ is MeO or Me;
$R^5$ is H or Me;
$R^6$ is Me or Et;
$R^7$ is H or $C_1$-$C_4$ alkyl;
$R^8$ and $R^9$ are independently H, ($C_1$-$C_4$)alkyl, $CH_2OH$, or $CH_2O(C_1$-$C_4)$alkyl, or $R^8$ and $R^9$ combine to form $(CHR^{10})_m$;
each $R^{10}$ is independently H, OH, O($C_1$-$C_4$)alkyl, or ($C_1$-$C_4$)alkyl;
Ar is an unsubstituted or substituted aromatic moiety selected from the group consisting of phenyl,

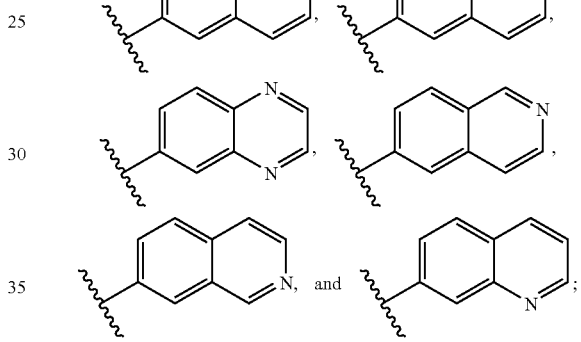

wherein a substituted aromatic moiety Ar has one to three substituents independently selected from the group consisting of halo, hydroxy, $C_1$-$C_4$ alkyl, $C_2$-$C_4$ alkenyl, $C_2$-$C_4$ alkynyl, trifluoromethyl, cyano, nitro, $C_1$-$C_3$ alkylamino or dialkylamino, and $C_1$-$C_3$ alkoxy; and $Ar^1$ is phenyl or phenyl substituted with one to three substituents independently selected from the group consisting of halo, hydroxy, $C_1$-$C_4$ alkyl, $C_2$-$C_4$ alkenyl, $C_2$-$C_4$ alkynyl, trifluoromethyl, cyano, nitro, $C_1$-$C_3$ alkylamino or dialkylamino, and $C_1$-$C_3$ alkoxy;

m is 1, 2, 3, or 4; and
n is 0, 1, or 2;
subject to
a first proviso (I) that when (a) $R^1$ is other than

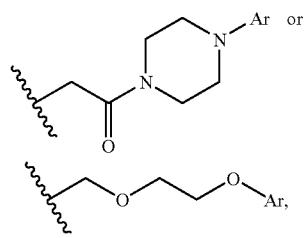

(b) $R^2$ is CHO, and (c) $R^3$ is other than

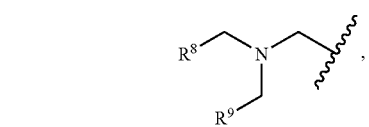

then Ar is other than unsubstituted or substituted phenyl; and a second proviso (II) that when (a) $R^1$ is H and (b) $R^2$ is CHO, then $R^3$ is

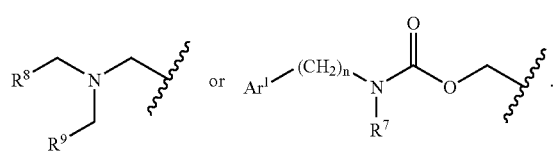

2. A compound according to claim 1, wherein $R^1$ is selected from the group consisting of

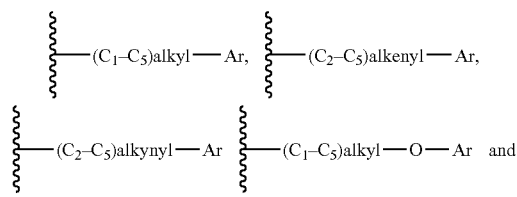

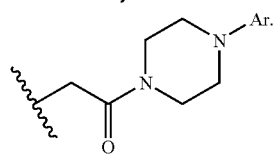

3. A compound according to claim 1, wherein $R^1$ is selected from the group consisting of

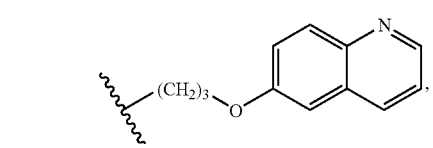

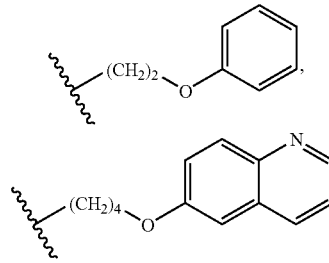

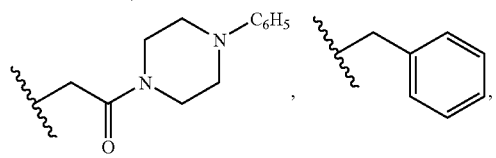

-continued

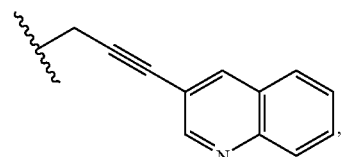

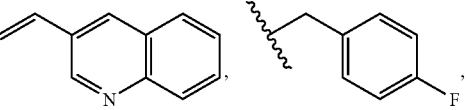

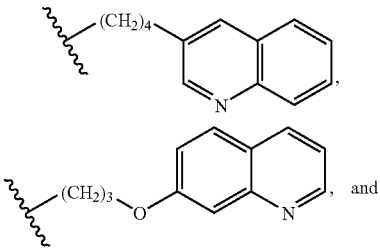

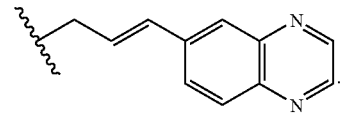

4. A compound according to claim 1, wherein $R^2$ is CHO or

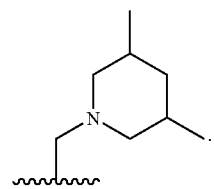

5. A compound according to claim 1, wherein $R^3$ is H, $CH_2OH$, $CH_2NMe_2$, or

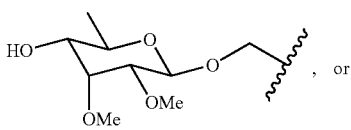

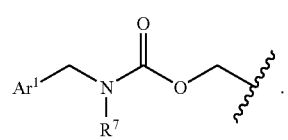

6. A compound according to claim 1, having a structure according to formula Ia

7. A compound according to claim 1, having a structure according to formula Ib
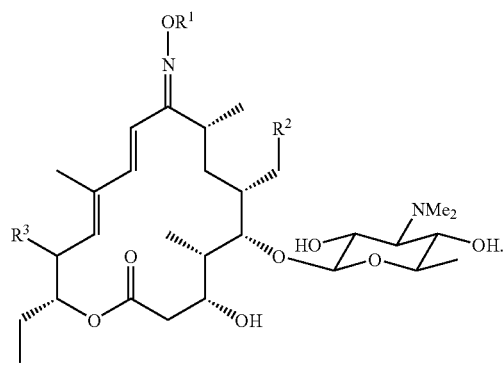
(Ia)
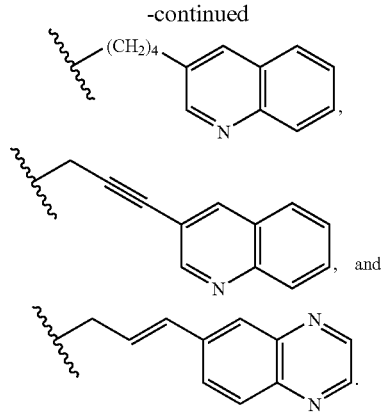
9. A compound according to claim 1, having a structure according to formula Ic
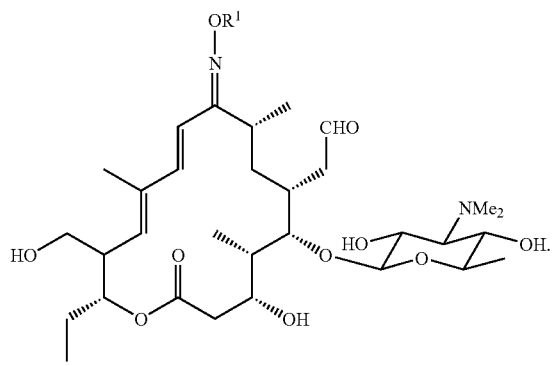
(Ib)
(Ic)
8. A compound according to claim 7, wherein $R^1$ is selected from the group consisting of
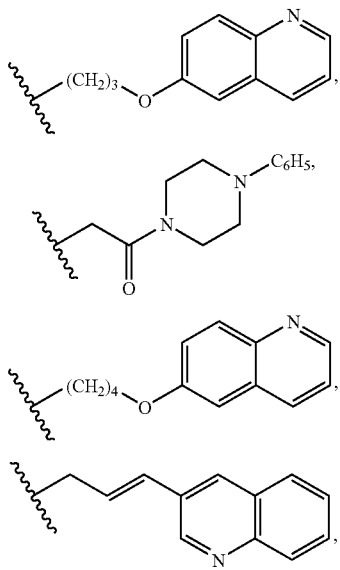
10. A compound according to claim 9, wherein $R^1$ is selected from the group consisting of
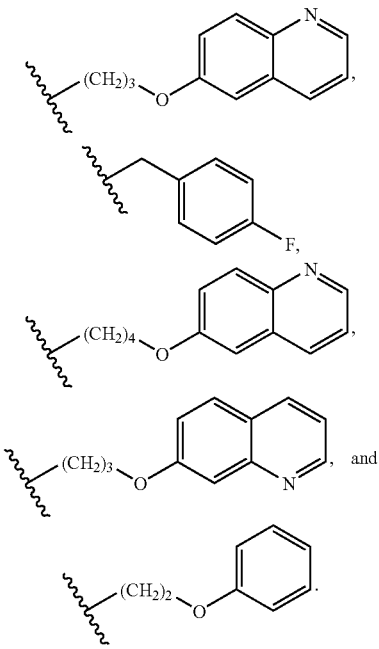

11. A compound according to claim 1, having a structure according to formula Id

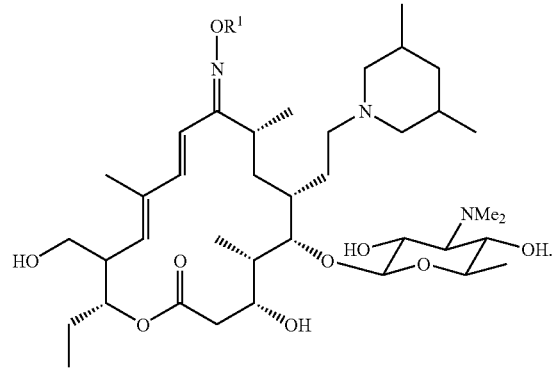
(Id)

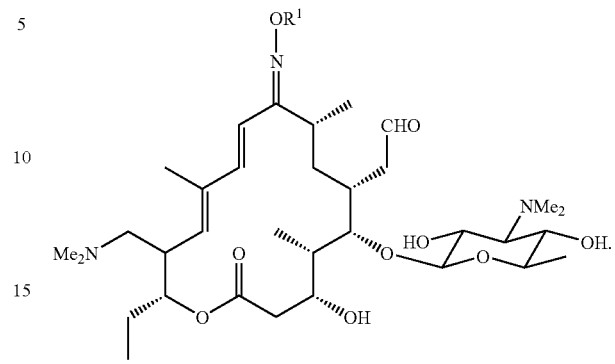
(Ie)

14. A compound according to claim 13, wherein $R^1$ is

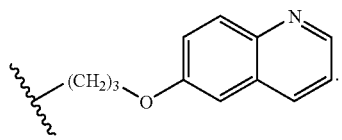

12. A compound according to claim 11, wherein $R^1$ is selected from the group consisting of

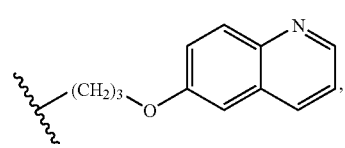

15. A compound according to claim 1, having a structure according to formula If

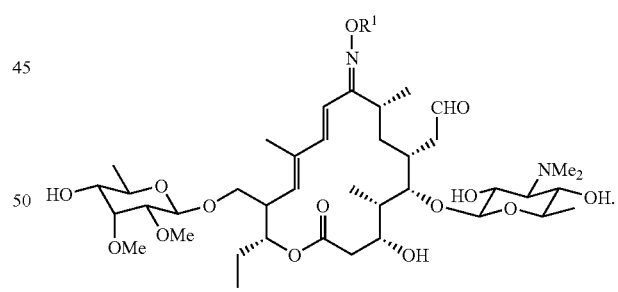
(If)

16. A compound according to claim 15, wherein $R^1$ is

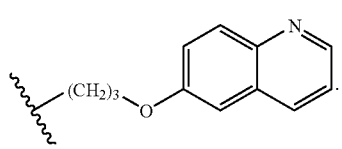

13. A compound according to claim 1, having a structure according to formula Ie

17. A compound according to claim 1, having a structure according to formula Ig

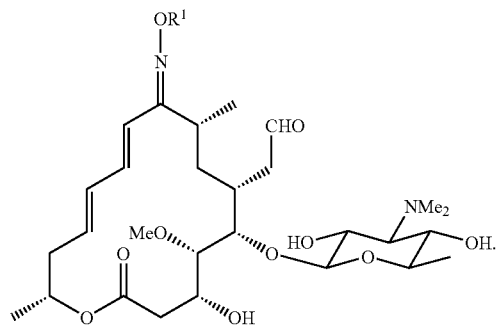
(Ig)
18. A compound according to claim 17, wherein $R^1$ is
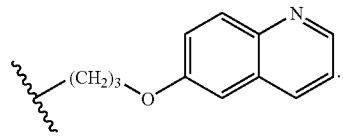
19. A compound according to claim 1, having a structure according to formula Ih:
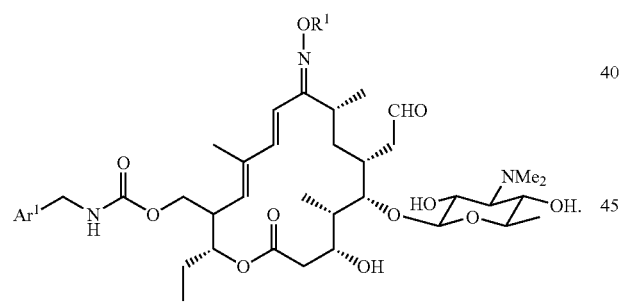
(Ih)
20. A compound according to claim 19, wherein $Ar^1$ is phenyl.
21. A compound according to claim 19, wherein $R^1$ is selected from the group consisting of H,
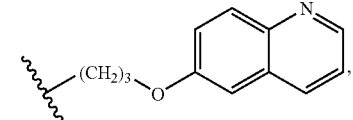
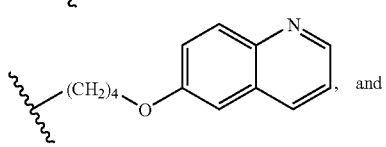
and
-continued
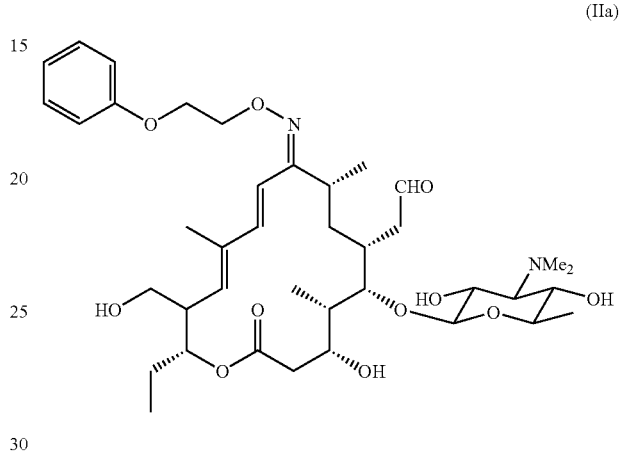
22. A compound having a structure according to formula IIa, IIb, IIc, or IId:
(IIa)
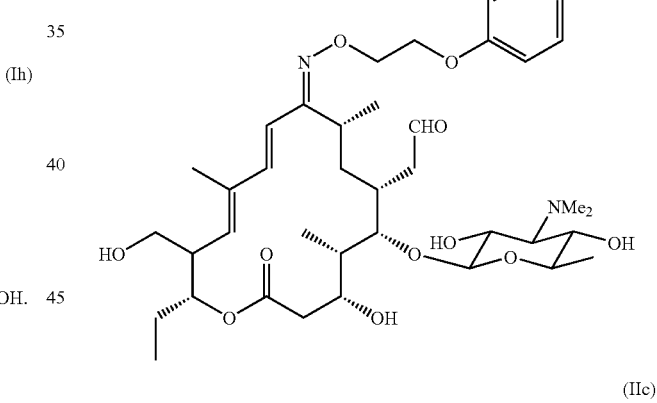
(IIb)
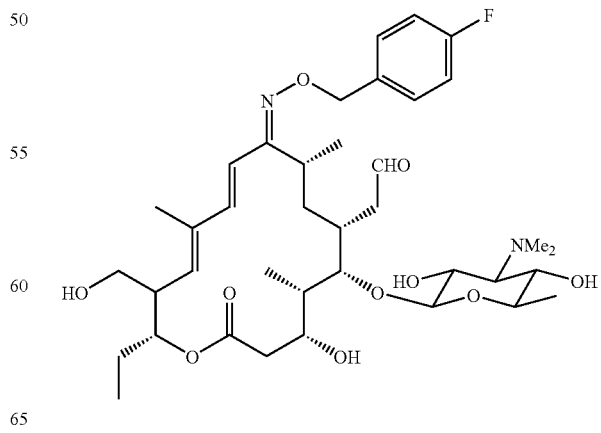
(IIc)

-continued (IId)

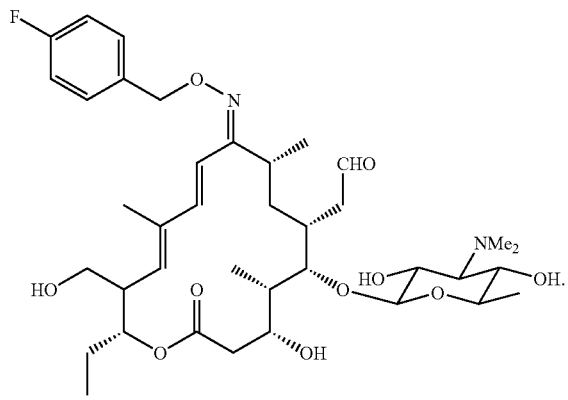

and the pharmaceutically acceptable salts thereof.

23. A method for treating a bacterial infection, comprising administering to a subject suffering from such infection a therapeutically effective amount of a compound according to claim 1.

24. A method according to claim 23, wherein the subject is a human.

25. A method according to claim 23, wherein the subject is a non-human mammal.

26. A method for inhibiting the proliferation of bacteria, comprising contacting the bacteria with an effective amount of a compound according to claim 1.

27. A pharmaceutical formulation comprising a compound according to claim 1 and an excipient.

* * * * *